US011391711B2

(12) United States Patent
Shao et al.

(10) Patent No.: US 11,391,711 B2
(45) Date of Patent: Jul. 19, 2022

(54) GOLD/QUANTUM DOT NANOPROBE FOR DETECTING ACTIVE RICIN IN COMPLEX MATRIX AND APPLICATION THEREOF

(71) Applicant: BEIJING CENTER FOR DISEASE PREVENTION AND CONTROL, Beijing (CN)

(72) Inventors: Bing Shao, Beijing (CN); Jiefang Sun, Beijing (CN); Jing Zhang, Beijing (CN)

(73) Assignee: BEIJING CENTER FOR DISEASE PREVENTION AND CONTROL, Beijing (CN)

( * ) Notice: Subject to any disclaimer, the term of this patent is extended or adjusted under 35 U.S.C. 154(b) by 0 days.

(21) Appl. No.: 17/310,020

(22) PCT Filed: Jan. 15, 2020

(86) PCT No.: PCT/CN2020/072143
§ 371 (c)(1),
(2) Date: Jan. 5, 2022

(87) PCT Pub. No.: WO2020/147735
PCT Pub. Date: Jul. 23, 2020

(65) Prior Publication Data
US 2022/0137020 A1   May 5, 2022

(30) Foreign Application Priority Data
Jan. 17, 2019   (CN) .................. 201910042764.X

(51) Int. Cl.
*A61K 9/00*   (2006.01)
*G01N 33/10*   (2006.01)
(Continued)

(52) U.S. Cl.
CPC ......... *G01N 33/10* (2013.01); *G01N 21/6428* (2013.01); *G01N 33/533* (2013.01);
(Continued)

(58) Field of Classification Search
CPC ....................................... G01N 33/10
See application file for complete search history.

(56) References Cited

U.S. PATENT DOCUMENTS

| 2011/0294116 A1* | 12/2011 | Huang ................ C12Q 1/6869 435/6.1 |
| 2013/0295563 A1 | 11/2013 | Nam et al. |
| CN 101206224 | 6/2008 | |
| CN 101498733 | 8/2009 | |
| CN 101545905 | 9/2009 | |

FOREIGN PATENT DOCUMENTS

| CN | 1590406 A | 3/2005 |
| CN | 1970573 A | 5/2007 |

(Continued)

OTHER PUBLICATIONS

Sun, Ultrasensitive On-Site Detection of Biological Active Ricin in Complex Food Matrices Based on Immunomagnetic Enrichment and Fluorescence Switch-On Nanoprobe, Anal. Chem., 2019, 91, 10, 6454-6461 (Year: 2019).*

(Continued)

*Primary Examiner* — Paul W Dickinson
(74) *Attorney, Agent, or Firm* — Novick, Kim & Lee, PLLC; Allen Xue

(57) ABSTRACT

The present disclosure discloses a gold/quantum dot nanoprobe for detecting active ricin in a complex matrix and application thereof. The gold/quantum dot nanoprobe is a nanoprobe formed by utilizing gold nanoparticles and quantum dots, which are modified by single strand oligodeoxynucleotides (ssODN), to form double strand oligodeoxynucleotides in a base pairing hybridizing mode and
(Continued)

assembling the gold nanoparticles and the quantum dots into a core-satellite structure. According to the present disclosure, the gold/quantum dot nanoprobe is used for detecting the active ricin, has a limit of detection of 7.46 ng/mL, is high in accuracy and good in reliability, and does not require large-scale equipment and complex operations. In order to further eliminate the false positive result, the present disclosure further provides a method for enriching ricin in a complex sample by utilizing magnetic beads. In a case that specific active ricin concentration does not need to be known, the gold/quantum dot nanoprobe provided by the present disclosure can implement naked eye visual detection by the quenched and switch-on operations of fluorescence.

10 Claims, 9 Drawing Sheets

Specification includes a Sequence Listing.

(51) Int. Cl.
| | | |
|---|---|---|
| *G01N 21/64* | (2006.01) | |
| *G01N 33/533* | (2006.01) | |
| *G01N 33/543* | (2006.01) | |
| *G01N 33/58* | (2006.01) | |
| *B82Y 5/00* | (2011.01) | |
| *B82Y 20/00* | (2011.01) | |
| *B82Y 30/00* | (2011.01) | |
| *B82Y 40/00* | (2011.01) | |

(52) U.S. Cl.
CPC ..... *G01N 33/54326* (2013.01); *G01N 33/582* (2013.01); *G01N 33/587* (2013.01); *B82Y 5/00* (2013.01); *B82Y 20/00* (2013.01); *B82Y 30/00* (2013.01); *B82Y 40/00* (2013.01); *G01N 2021/6432* (2013.01); *G01N 2021/6439* (2013.01)

(56) References Cited

FOREIGN PATENT DOCUMENTS

| CN | 101561434 A | 10/2009 |
|---|---|---|
| CN | 101609091 A | 12/2009 |
| CN | 101676727 A | 3/2010 |
| CN | 101698889 A | 4/2010 |
| CN | 201522493 U | 7/2010 |
| CN | 101980023 A | 2/2011 |
| CN | 102020714 A | 4/2011 |
| CN | 102534013 A | 7/2012 |
| CN | 104849254 A | 8/2015 |
| CN | 109852673 A | 6/2019 |

OTHER PUBLICATIONS

Li, Yaqi et al.; Study on Novel Detection Method for GM Soybean Based on Quantum Dots; China Doctoral Dissertation Full-text Database, I140-42, Jan. 15, 2018, Chapters.

Tang, Jijun et al.; New Surface-Enhanced Raman Sensing Chip Designed for On-Site Detection of Active Ricin in Complex Matrices Based on Specific Depurination; ACS Applied Materials & Interfaces, Jan. 27, 2016, pp. 2449-2455.

Sun, Jiefang et al.; Fast on-Site Visual Detection of Active Ricin Using a Combination of Highly Efficient DualRecognition Affinity Magnetic Enrichment and a Specific Gold Nanoparticle Probe, American Chemical Society, 2017, 89, pp. 12209-12216.

Sturm, Matthew B. et al.; Detecting Ricin: Sensitive Luminescent Assay for Ricin A-Chain Ribosome Depurination Kinetics; Analytical Chemistry, vol. 81, No. 8, Apr. 15, 2009, pp. 2847-2853.

Bevilacqua, Vicky L.H. et al.; Ricin Activity Assay by Direct Analysis in Real Time Mass Spectrometry Detection of Adenine Release, Analytical Chemistry, vol. 82, No. 3, Feb. 1, 2010, pp. 798-800.

Kalb, Suzanne R. et al.; Mass Spectrometric Detection of Ricin and its Activity in Food and Clinical Samples, Analytical Chemistry, vol. 81, No. 6, Mar. 15, 2009, pp. 2037-2042.

Wang, Dongxia et al.; Improved Sensitivity for the Qualitative and Quantitative Analysis of Active Ricin by MALDI-TOF Mass Spectrometry, Analytical Chemistry, 2016, 88, pp. 6867-6872.

* cited by examiner

P1(a)-AuNPs

P2(a)-QDs

AuNPs/QDs

SEQUENCE LISTING

```
<160> NUMBER OF SEQ ID NOS: 9

<210> SEQ ID NO 1
<211> LENGTH: 18
<212> TYPE: DNA
<213> ORGANISM: Artificial Sequence
<220> FEATURE:
<223> OTHER INFORMATION: synthesized

<400> SEQUENCE: 1
ttttttttta tatatata                                                    18

<210> SEQ ID NO 2
<211> LENGTH: 15
<212> TYPE: DNA
<213> ORGANISM: Artificial Sequence
<220> FEATURE:
<223> OTHER INFORMATION: synthesized

<400> SEQUENCE: 2
tttttttata tatat                                                       15

<210> SEQ ID NO 3
<211> LENGTH: 21
<212> TYPE: DNA
<213> ORGANISM: Artificial Sequence
<220> FEATURE:
<223> OTHER INFORMATION: synthesized

<400> SEQUENCE: 3
tttttttttt ttctatatat a                                                21

<210> SEQ ID NO 4
<211> LENGTH: 21
<212> TYPE: DNA
<213> ORGANISM: Artificial Sequence
```

```
<220> FEATURE:
<223> OTHER INFORMATION: synthesized

<400> SEQUENCE: 4
taacataatt aggtctttt t                                              21

<210> SEQ ID NO 5
<211> LENGTH: 18
<212> TYPE: DNA
<213> ORGANISM: Artificial Sequence
<220> FEATURE:
<223> OTHER INFORMATION: synthesized

<400> SEQUENCE: 5
tatcagtctg actttttt                                                 18

<210> SEQ ID NO 6
<211> LENGTH: 21
<212> TYPE: DNA
<213> ORGANISM: Artificial Sequence
<220> FEATURE:
<223> OTHER INFORMATION: synthesized

<400> SEQUENCE: 6
tagcatattc tggcatttt t                                              21

<210> SEQ ID NO 7
<211> LENGTH: 36
<212> TYPE: DNA
<213> ORGANISM: Artificial Sequence
<220> FEATURE:
<223> OTHER INFORMATION: synthesized

<400> SEQUENCE: 7
gacctaatta tgaaaaaaaa aaaattatat atatat                             36

<210> SEQ ID NO 8
<211> LENGTH: 39
<212> TYPE: DNA
<213> ORGANISM: Artificial Sequence
<220> FEATURE:
<223> OTHER INFORMATION: synthesized

<400> SEQUENCE: 8
gtcagactga taaaaaaaaa aaaaaaaaaa atatatata                          39

<210> SEQ ID NO 9
<211> LENGTH: 33
<212> TYPE: DNA
<213> ORGANISM: Artificial Sequence
<220> FEATURE:
<223> OTHER INFORMATION: synthesized

<400> SEQUENCE: 9
tgccagaata tgaaaaaaaa actatatata tag                                33
```

GOLD/QUANTUM DOT NANOPROBE FOR DETECTING ACTIVE RICIN IN COMPLEX MATRIX AND APPLICATION THEREOF

INCORPORATION OF SEQUENCE LISTING

This application contains a sequence listing submitted in Computer Readable Form (CRF). The CFR file containing the sequence listing entitled "PA668-0002_ST25.txt", which was created on Jul. 9, 2021, and is 2,024 bytes in size. The information in the sequence listing is incorporated herein by reference in its entirety.

FIELD

The present disclosure relates to a detection method of natural toxins, in particular to a rapid, visual, simple and convenient detection method of active ricin, and a gold/quantum dot nanoprobe for the method.

BACKGROUND

Ricin is a highly lethal natural toxin, belongs to type II ribosome-inactivating proteins, has the relative molecular mass of about 64,000 Da, is formed by linking two A and B polypeptide chains by a disulfide bond, has ultrahigh cytotoxicity (the toxicity of the ricin is 385 times of that of an organophosphorus nerve agent VX, 6,000 times of that of a cyanide and 10,000 times of that of a botulinum toxin), and can cause serious poisoning of an organism by the way of inhalation, oral administration or intravenous injection. The ricin widely exists in the seeds of *Ricinus communis* and has the characteristics of easiness for extraction, stable properties, simplicity and convenience for poisoning and the like, and currently, it is still lack of effective prevention or treatment means for the ricin, so the ricin is frequently used for assassination and terrorist attack activities. Due to the characteristics of the ricin, in the control list 1 of the Chemical Weapons Convention (CWC) and Biological Weapons Convention (BWC), the ricin is a unique protein ricin. Existing detection methods of the ricin in food and environment samples include an immunoassay method (enzyme immunoassay and colloidal gold immunoassay test paper) and a mass spectrometric detection method; the former is high in sensitivity, but has a high false positive rate; and the latter can implement confirmation and quantitative analysis of the ricin, but is highly depended on instrument equipment and unsuitable for rapid detection on the emergency guarantee site. Moreover, all the technologies above cannot determine whether toxins in the samples still have bioactivity. Different from a case that chemical warfare agents only need to be subjected to rapid qualitative and quantitative analysis, in the actual monitoring process of this category of biochemical warfare agents, once it is determined that a contaminated sample contains the ricin, what people ultimately care about are whether the ricin has bioactivity (toxicity) and whether the ricin will form a threat to health of people. In 2009, the first ricin international joint test summary report hosted by German Robert Koch research institute clearly points out that: how to detect active ricin is a difficult problem which urgently needs to be solved.

In the activity analysis research of the ricin, mainly a method for measuring LD50 on the basis of an animal test and a method for measuring IC50 on the basis of a cytotoxicity test are adopted in the early period, these methods are troublesome, time-consuming and strict in condition, cannot complete activity detection of residual toxins in a real sample, and thus are only used as conventional methods for representing activities of toxins. With the continuous deepening of understanding of people for the ricin, some novel activity analysis methods are developed in recent years. The toxication mechanism of the ricin can be summarized as follows: a toxin B chain with the agglutinin activity contains two galactose residue binding sites, and can be bound with glycoprotein or glycolipid containing the galactose residue on the cell surfaces to promote toxin molecules to invaginate to enter cells, an interchain disulfide bond is reduced to dissociate out an A active chain, and the A chain plays the activity of N-glycosidase to enable adenine at specific positions of 28S rRNA of a 60S subunit of a ribosome to be hydrolyzed, resulting in that the ribosome is inactivated, so that protein synthesis is inhibited to cause cell death. Based on this mechanism, some reports try to implement activity identification by detection on the activity of glycosidase of a ricin A chain, and the basic idea is that: the ricin and the ribosome RNA or an oligonucleotide substrate (RNA or DNA) with a specific structure are incubated under the in-vitro condition, and the amount of adenine released in a depurination reaction is quantitatively measured by utilizing mass spectrometry, or after the adenine is treated by an enzyme and the like and subjected to multi-step derivation, radiolabelling, colorimetric detection or fluorescence detection, so that indirect evaluation on the activity of the ricin is implemented. These methods all can be well applied to activity analysis on the toxins and are accurate in quantification and high in sensitivity, but due to the limitations of expensive instruments, troublesome steps, strong technicality and the like, it is difficult for the methods to apply to on-site rapid detection on the active toxins in special environments such as war, emergencies and the like.

Tang, et al. (ACS Appl. Mater. Interfaces. 2016, 8, 2449-2455) disclosed construction of a sensing system on the basis of a depurination reaction between ricin and a specific oligonucleotide substrate poly-21dA linked onto a surface enhanced raman scattering (SERS) substrate. The poly-21dA has a very strong Raman signal, and thus can serve as a Raman report element, and meanwhile, also serves as a specific reaction element for SERS detection. Based on excellent linear dependence between the ricin concentration and the SERS intensity, high sensitive detection on the ricin can be implemented. The method can implement rapid surface enhanced Raman detection on the active ricin in tap water, fruit juice and a diluted serum sample, but cannot be applied to detection on low-sensitivity active toxins in more complex matrices such as foods and the like, and still has a large improvement space in the aspects of matrix applicability and sensitivity.

In order to solve this problem, another document (Anal. Chem. 2017, 89, 12209-12216) of the inventor disclosed a rapid detection method of active ricin. The method combines a magnetic sample pretreatment technology with a gold nanoprobe. An SERS effect is caused after the gold nanoprobes (AuNPs) are aggregated, and an obvious change, which is caused by the depurination reaction of the active ricin on a substrate sequence on a nano interface, of a characteristic peak of the substrate sequence is detected so as to implement sensing. AuNPs of which the surfaces are modified with a specific ssDNA substrate sequence are prepared, then the AuNPs are deposited on a Si chip by utilizing the aggregation effect of sulfate on nanoparticles, and due to the shortening of the distance between the nanoparticles or aggregation of the nanoparticles, it will be caused that a sensitive SERS enhanced signal appears on surface ssDNA. "Internal standard molecules" with the Raman activity and the substrate sequence are modified jointly on the surfaces of the AuNPs, and the ssDNA characteristic peak for quantification is corrected by a characteristic Raman signal of the internal standard molecules so as to implement quantitative analysis on active target molecules. However, detection on the Raman signal is still time-consuming and labor-consuming, and has high requirements for equipment and operators.

SUMMARY

In order to solve the above-mentioned problems in the prior art, the present disclosure carries out research and improvement on how to rapidly detect active ricin in a complex matrix, and eliminates the frequently generated false positive problem in a common method; and further, in the practical application, in case of emergency, the ricin can be simply and conveniently detected in field without using large-scaled complex equipment, and an ideal situation is to provide a method for visually and rapidly detecting the ricin.

In order to facilitate understanding and consider the length, the present disclosure uses the following abbreviations to represent the specific technical meanings:

| | |
|---|---|
| ricin: ricin | $mAb_{ricin}$: ricin monoclonal antibody |
| AuNPs: gold nanoparticles | QDs: quantum dots |
| MB: magnetic bead | ssODN: single strand oligodeoxynucleotides |
| dsODN: double strand oligodeoxynucleotides | CBMAA: 3-((3-methacrylateaminopropyl) dimethyl ammonio)-propionate |
| CTA: propyl-4-(trimethoxysilyl) benzyl sulfocarbonate | HEMA: 2-hydroxyethyl methacrylate |
| P(C-H): polymer brushes obtained by carrying out copolymerization on CBMAA and HEMA which serve as monomers through an RAFT reaction | MB@P(C-H): magnetic beads grafted with polymer brushes P(C-H) |
| MB@P(C-H)-$mAb_{ricin}$: magnetic beads adsorbing the ricin monoclonal antibody on the polymer brushes | |

In order to solve the above-mentioned technical problem, a first objective of the present disclosure is that:

A gold/quantum dot nanoprobe for detecting active ricin includes gold nanoparticles modified by a linker P1 containing single strand oligodeoxynucleotides (P1-AuNPs), quantum dots modified by a linker P2 containing single strand oligodeoxynucleotides (P2-QDs) and single strand oligodeoxynucleotides P3; the P1, the P2 and the P3 form double strand oligodeoxynucleotides by base pairing hybridization; the gold nanoparticles and the quantum dots are linked to be assembled into a core-satellite structure with the gold nanoparticles being a core and the quantum dots surrounding the gold nanoparticle core.

Specifically, the linkers P1 and P2 independently contain 15 to 33, preferably 18 to 30, deoxynucleotide units, the P3 contains 30 to 48, preferably 33 to 42, deoxynucleotide units, sequences of deoxynucleotides subjected to pairing hybridization with the P1 and P2 are positioned at both ends of the P3, and a sequence of 9 to 21, preferably 12 to 15, deoxynucleotides of which a base is adenine (A) is positioned in the middle of the P3.

Further, a 5' terminal of the P1 is sulfydryl and is linked with the surfaces of gold nanoparticles AuNPs to obtain the P1 modified gold nanoparticles (P1-AuNPs), while a 3' terminal is a deoxynucleotide sequence L1; a 3' terminal of the P2 is amino and is linked with quantum dots QDs to obtain the P2 modified quantum dots (P2-QDs), while a 5' terminal is a deoxynucleotide sequence L2; the P1 and P2 are respectively subjected to pairing hybridization with the deoxynucleotide sequences L1' and L2' at both ends of the P3 through the sequences L1 and L2 to form a double strand structure to link the AuNPs and the QDs.

Further, a condensed structural formula of the linker P1 is 5'-SH-alkylene-poly($dT_{n1}$)-L1-3', a condensed structural formula of the linker P2 is 5'-L2-poly($dT_{n2}$)-alkylene-$NH_2$-3', and a condensed structural formula of the linker P3 is 3'-L1'-poly($dA_{n3}$)-L2'-5', wherein the number of carbon atoms of alkylene is an integer within a range of 4 to 12 and preferably is an integer within a range of 6 to 9; poly($dT_{n1}$) and poly($dT_{n2}$) represent sequences containing a certain number of deoxynucleotides of which a base is thymine (T), and n1 and n2 represent numbers of deoxynucleotides of which the base is the thymine (T) and are independently 6 to 15, preferably 9 to 12; poly($dA_{n3}$) represents a chain of a certain number of deoxynucleotides of which the base is the adenine (A), and n3 represents a number of deoxynucleotides of which the base is the adenine (A), and is an integer within a range of 9 to 21 and preferably is an integer within a range of 12 to 18; L1 represents a sequence of 6 to 15, preferably 9 to 12, deoxynucleotides, wherein the number of the deoxynucleotides of which the base is the adenine (A) is at least 40%, and the number of the oligodeoxynucleotides of which the base is the thymine (T) is at least 40%; and L2 represents a sequence of 9 to 18, preferably 12 to 15, deoxynucleotides.

In a preferred technical solution of the present disclosure, in the L1, the deoxynucleotides of which the base is the adenine (A) and the deoxynucleotides of which the base is the thymine (T) are alternately arranged to form a sequence of . . . ATATATAT . . . .

In a preferred technical solution of the present disclosure, the sequence L1' at one end of the P3 not only is subjected to pairing hybridization with the sequence L1 of the P1, but also is subjected to pairing hybridization with one part of the L2 of the P2.

The law of base pairing hybridization mentioned in the present disclosure is well known in the art, i.e., the adenine (A) and the thymine (T) are complementarily paired, and guanine (G) and cytosine (C) are complementarily paired.

In preferred embodiments of the present disclosure, the P1, the P2 and the P3 respectively have structures shown in Table 1:

TABLE 1

| | |
|---|---|
| P1(a) | 5'-SH-$C_6H_{12}$-TTT TTT TTT <u>ATA TAT ATA</u> (SEQ ID NO: 1)-3' |
| P1(b) | 5'-SH-$C_{10}H_{20}$-TTT TTT <u>TAT ATA TAT</u> (SEQ ID NO: 2)-3' |
| P1(c) | 5'-SH-$C_5H_{10}$-TTT TTT TTT TTT <u>CTA TAT ATA</u> (SEQ ID NO: 3)-3' |
| P2(a) | 5'-TAA CAT AAT TAG GTC TTT TTT (SEQ ID NO: 4)-$C_6H_{12}$-$NH_2$-3' |
| P2(b) | 5'-TAT CAG TCT GAC TTT TTT (SEQ ID NO: 5) $C_8H_{16}$-$NH_2$-3' |
| P2(c) | 5'-TAG CAT ATT CTG GCA TTT TTT (SEQ ID NO: 6)-$C_6H_{12}$-$NH_2$-3' |

TABLE 1-continued

| | |
|---|---|
| P3(a) | 5'-GAC CTA ATT ATG AAAAAAAAAAAA TTA <u>TAT ATA TAT</u> (SEQ ID NO: 7)-3' |
| P3(b) | 5'-GTC AGA CTG ATA AAAAAAAAAAAAAAAAA <u>ATA TAT ATA</u> (SEQ ID NO: 8)-3' |
| P3(c) | 5'-TGC CAG AAT ATG AAAAAAAAA CTA <u>TAT ATA TAG</u> (SEQ ID NO: 9)-3' |

In Table 1, the bases of the underlined part of the P1 and the bases of the underlined part of the P3 are subjected to pairing hybridization to form the double strand structure, and the bases of the bold part of the P2 and the bases of the bold part of the P3 are subjected to pairing hybridization to form the double strand structure.

According to the present disclosure, by special design on the structures of the linkers P1, P2 and P3, after the pairing hybridization reaction among the linkers, the sequence of 9 to 21 continuously arranged deoxynucleotides of which the base is the adenine (A), i.e., poly($dA_{n3}$), on the P3 forms a loop-shaped flexible structure, so that the AuNPs and the QDs are close to each other. Due to the strong dipole-metal interaction (nano surface energy transfer), the fluorescence of the QDs is quenched, i.e., there is a phenomenon that the intensity of a fluorescence characteristic peak of the QDs at 575 nm is greatly reduced. In the presence of active ricin, several adenines (A) may be cut both from the loop-shaped poly($dA_{n3}$) sequence of the P3 and the double strand sequence formed by the P1 and the P2 on the AuNPs/QDs, and then the P2-QDs are triggered to be dissociated from the P1-AuNPs, so that the fluorescence of the QDs is not quenched any more, and the intensity of the fluorescence characteristic peak at 575 nm is gradually increased. The concentration of the active ricin can be known by detecting the fluorescence intensity at this position. In a case that the concentration of the active ricin does not need to be known exactly, when it is monitored that the fluorescence intensity in a system is a switch-on state (i.e., the fluorescence intensity exceeds a certain threshold), it can be known that there is the active ricin in a sample.

The gold/quantum dot nanoprobe and a ricin detection principle thereof will be further illustrated as follows by the means of FIG. 1 and FIG. 2:

FIG. 1 is a schematic diagram in which deoxynucleotide chains on an AuNPs/QDs nanoprobe form a double strand structure to link the AuNPs and the QDs.

The P1 is
5'-SH-$C_6H_{12}$-TTT TTT TTT <u>ATA TAT ATA</u>-3',
i.e., P1 (a);

The P2 is 5'-TAA CAT AAT TAG GTC TTT
TTT-$C_6H_{12}$-$NH_2$-3',
i.e., P2 (a);

The P3 is 5'-GAC CTA ATT ATG
AAAAAAAAAAAA TTA <u>TAT ATA TAT</u>-3',
i.e., P3 (a);
and The bases of the underlined part of the P1 and the bases of the underlined part of the P3 are subjected to pairing hybridization to form the double strand structure, and the bases of the bold part of the P2 and the bases of the bold part of the P3 are subjected to pairing hybridization to form the double strand structure. It can be seen from FIG. 1 that a sequence, close to the 3' terminal, on the P3, i.e., TTA <u>TATATATAT</u>, not only is subjected to pairing hybridization with <u>ATATATATA</u>-3' on the P1, but also is subjected to pairing hybridization with 5'-TAA on the P2. Such pairing hybridization mode enables the double strand structure formed by the P1, the P2 and the P3 to form a straight line so as to force poly($dA_{n3}$) on the P3 to form a flexible loop-shaped structure. Therefore, the AuNPs and the QDs are close to each other, and then the fluorescence is quenched.

FIG. 2 is a schematic diagram in which after the active ricin is added, the fluorescence of the AuNPs/QDs is converted into a switch-on state from a quenched state. Due to the specific depurination reaction activity of the ricin, the active ricin can cut several adenines (A) from the double strand structure of the AuNPs/QDs and particularly from poly($dA_{n3}$) on the P3, so that the double strand structure is dissociated, the AuNPs and the QDs are separated from each other, and the quenching effect cannot be generated, and thus, the fluorescence intensity is switched on again.

Based on the principle above, a second objective of the present disclosure is to provide a method for detecting active ricin in a sample by using the gold/quantum dot nanoprobe, including the following steps of:

(S1) After performing a sufficient reaction on a gold/quantum dot nanoprobe solution and each active ricin with a known concentration, testing fluorescence intensity of the solutions, drawing a standard curve of a logarithm of the concentration of the active ricin and fluorescence intensity at 575 nm ($I_{575}$) in the sample, and obtaining a linear relationship formula between the logarithm of the concentration of the active ricin and the fluorescence intensity at 575 nm in the sample; and (S2) After adding the gold/quantum dot nanoprobe into a sample solution to be subjected to a sufficient reaction, monitoring fluorescence intensity at 575 nm in the solution, and calculating to obtain the concentration of the active ricin in the sample according to the standard curve in the step (S1).

Specifically, the method is implemented by the following technical solution:

One hour after the active ricin is added into the gold/quantum dot nanoprobe (AuNPs/QDs) solution, the concentration of the active ricin can be obtained by monitoring the fluorescence intensity at 575 nm in the solution.

Firstly, the standard curve of the concentration (ng/mL) of the active ricin and the fluorescence intensity at 575 nm ($I_{575}$) in the solution is established. Specifically, the AuNP/QD nanoprobe (535 nm, 0.5 OD) reacts with each active ricin with the known concentration (10 to 100 ng/mL) in an ammonium acetate buffer solution with a pH of 3.8 to 4.2 in a 96-well plate. Incubation is carried out for 2 hours at the temperature of 38° C., the fluorescence intensity of the solutions is tested, and drawing is carried out with the logarithm of the concentration of the active ricin and the fluorescence intensity at 575 nm, and the following formula is obtained by the linear relationship of the curve:

$$I_{575} = X \cdot lgC - Y$$

Wherein, 1575 represents the fluorescence intensity of the characteristic peak at 575 nm in the AuNPs/QDs solution, C represents the concentration of the active ricin, and the unit is ng/mL. X and Y are obtained by calculation after linear fitting is carried out on the curve. When each assembly of the AuNPs/QDs nanoprobe is assembled, i.e., a molar ratio of the P1-AuNPs to the P2-QDs to the P3 is fixed, and meanwhile, the concentration of the AuNPs/QDs nanoprobe is regulated to achieve the same optical density (OD) value, the values of X and Y are also fixed therewith. Therefore, the fluorescence intensity of the sample after the above-mentioned treatment at 575 nm is detected, and the concentration of the active ricin in the sample can be calculated by the formula above.

Whether the ricin exists in the sample can also be qualitatively judged by judging whether the fluorescence is switched on. For example, the AuNPs/QDs are added into a to-be-detected sample, after 2 hours, the sample is irradiated with an ultraviolet light flashlight in a dark place, and if the sample solution emits orange light, it is indicated that the active ricin with a certain concentration exists in the sample. That is because that if the active ricin exists in the sample, after the AuNPs/QDs nanoprobe is added, the fluorescence of the QDs can be switched on again, and at the moment, if the sample is irradiated with ultraviolet light, a photoluminescence phenomenon is generated, and light visible to naked eyes is generated. Therefore, by means of the AuNP/QD nanoprobe provided by the present disclosure, an effect of rapidly and visually detecting whether the ricin exists in the sample in field can be achieved only through the ultraviolet light flashlight without the help of other equipment.

Therefore, by means of the gold/quantum dot nanoprobe provided by the present disclosure, the concentration of the active ricin can be quantitatively detected through testing the fluorescence intensity in the sample, or whether the ricin exists in the sample can be qualitatively judged through judging whether the fluorescence is switched on. Based on the principle above, the present disclosure establishes a method for quantitatively/semi-quantitatively/qualitatively detecting the active ricin, which can flexibly select a detection mode according to actual demands and equipment conditions of the field so as to greatly enrich detection means and flexibility of the active ricin. The gold/quantum dot nanoprobe provided by the present disclosure shows very excellent effects in the aspects of accuracy, sensitivity, fouling resistance and limit of detection, has low requirements for the equipment and operators, is short in detection time, does not require large-sized equipment such as mass spectrometer and the like, and can implement accurate and rapid detection on the ricin in field.

However, it is found that due to strong electrostatic interaction between positively charged interfering proteins with the high concentration (5 μg/mL) and the negatively charged AuNP/QDs, aggregates are formed, resulting in influence on the accuracy of detection. Therefore, in a preferred technical solution of the present disclosure, before the AuNPs/QDs nanoprobe is adopted to carry out detection, a specific active ricin capture agent, i.e., MB@P(C-H)-mAb$_{ricin}$, is adopted firstly, after the active ricin is trapped and enriched under the action of a magnet, elution is carried out to obtain a purified active ricin solution, and then the AuNPs/QDs provided by the present disclosure are used for carrying out detection, so that monitoring accuracy is greatly promoted, and application of the AuNPs/QDs to detection on the active ricin in the complex sample is well expanded. FIGS. 3A and 3B are a schematic diagram of enrichment of the ricin.

Therefore, a third objective of the present disclosure is to provide a method for specifically enriching active ricin, including the following steps:

(I) Preparing ricin capture agent magnetic beads (MB@P(C-H)-mAb$_{ricin}$): 1) preparing magnetic beads NH$_2$-MBs, including a step of capping Fe$_3$O$_4$ with NH$_2$ modified SiO$_2$; 2) copolymerizing two monomers of 3-((3-methacrylateaminopropyl)dimethylammonio)-propionate (CBMAA) and 2-hydroxyethyl methacrylate (HEMA) through reversible addition-fragmentation chain transfer (RAFT) polymerization to form polymer brushes, and grafting the polymer brushes onto the magnetic beads NH$_2$-MBs to obtain MB@P(C-H), wherein MB represents the SiO$_2$-capped-Fe$_3$O$_4$ amine-modified magnetic beads, C represents 3-((3-methacrylateaminopropyl)dimethylammonio)-propionate (CBMAA), and H represents 2-hydroxyethyl methacrylate (HEMA); and 3) then covalently linking a ricin monoclonal antibody (mAb$_{ricin}$) and the MB@P(C-H) to obtain the ricin capture agent magnetic beads (MB@P(C-H)-mAb$_{ricin}$); and (II) Carrying out specific adsorption on the ricin in the sample by the ricin capture agent magnetic beads (MB@P(C-H)-mAb$_{ricin}$) for 20 min to 1 h, then enriching the magnetic beads to the bottom of a container by a magnet, and after pouring out a supernatant, adding an eluent to carry out elution, so that the ricin adsorbed on the magnetic beads is released again and enrichment of the active ricin is completed.

In the actual detection, firstly, the ricin in the sample may be subjected to specific adsorption by the ricin capture agent magnetic beads, then the magnetic beads are enriched to the bottom of the container by the magnet, and after the supernatant is poured out, the eluent is added to carry out elution, so that the ricin adsorbed on the magnetic beads is released again. Therefore, when detection is carried out, interference of substances such as various inorganic ions, organic matters, proteins and residues thereof and the like in the complex sample can be eliminated. By the excellent fouling resistance of the monomer 3-((3-methacrylateaminopropyl)dimethylammonio)-propionate (CBMAA), adsorption of impurities in the complex sample onto the surfaces of the polymer brushes is avoided, and by the specific adsorption of the active ricin by the ricin monoclonal antibody, the enriching and purifying process of the active ricin in the complex sample is completed, so that the objective of detecting a trace amount of ricin is achieved, and the false positive result possibly caused by the impurities in the subsequent detection is reduced.

The present disclosure achieves the beneficial effects that:

The active ricin is detected by the fluorescence quenched and switch-on process of the AuNPs/QDs. The concentration of the active ricin can be known only by monitoring the fluorescence intensity of the sample without the large-sized equipment. By tests, it is proved that the methods provided by the present disclosure are sensitive, reliable and short in time, and do not need to use large-sized instruments. Moreover, in some special occasions, there is no need to know the specific concentration of the ricin, but it only needs to judge whether the ricin exists, and the present disclosure provides a visual method capable of carrying out detection in field, so that whether the ricin exists can be known only by one ultraviolet light flashlight through detecting whether the sample is in the fluorescence switch-on state, and an effective method is provided for rapid naked eye detection on the ricin.

BRIEF DESCRIPTION OF THE DRAWINGS

FIG. 3A shows a synthesis process of ricin capture agent magnetic beads (MB@P(C-H)-mAb$_{ricin}$); and FIG. 3B is a schematic diagram in which elution is carried out after the MB@P(C-H)-mAb$_{ricin}$ carries out enrichment on the ricin.

FIG. 10A is a TEM diagram after 30 ng/mL of ricin is added; and FIG. 10B is a TEM diagram after 80 ng/mL of ricin is added.

DETAILED DESCRIPTION OF THE EMBODIMENTS

Figure 1:
FIG. 1 is a schematic diagram in which deoxynucleotide chains on an AuNPs/QDs nanoprobe form a double strand structure to link AuNPs and QDs.
Figure 2:
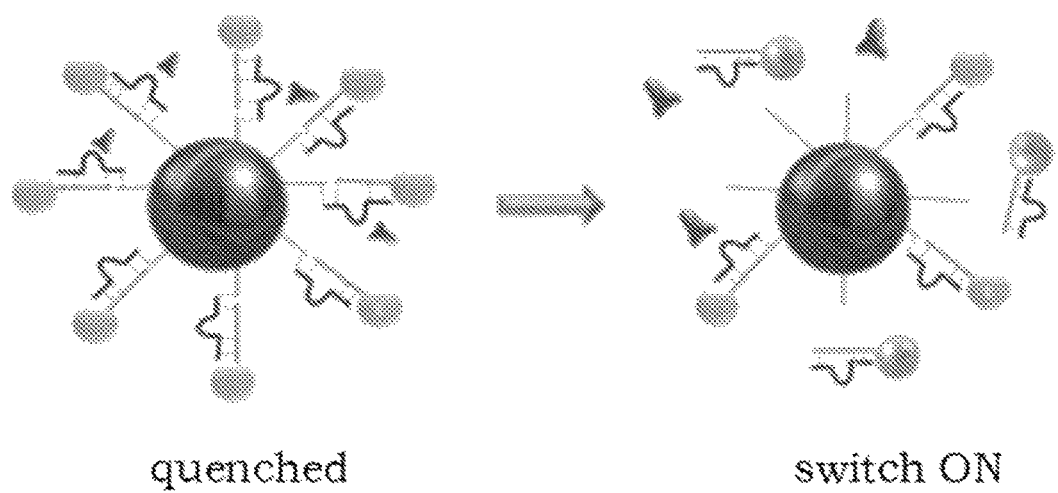
FIG. 2 is a schematic diagram in which after active ricin is added, fluorescence of the AuNPs/QDs is converted into a switch-on state from a quenched state.
Figure 3A:
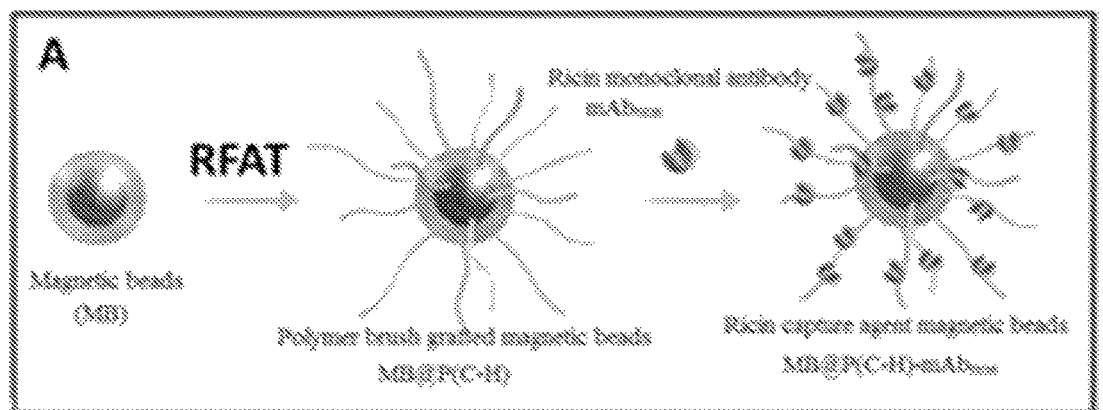
FIGS. 3A and 3B are schematic diagrams of enrichment of ricin.
Figure 3B:
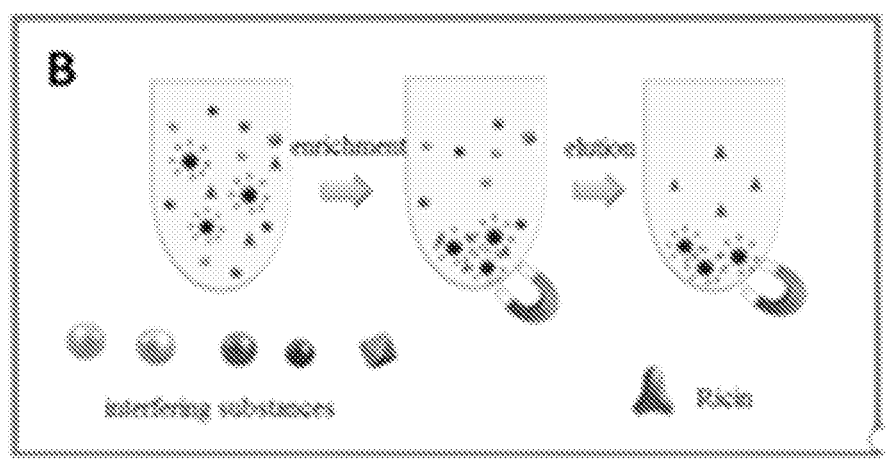

The present disclosure will be further illustrated in connection with the drawings and embodiments, the embodiments are implemented on the premise of the technical solutions of the present disclosure, the detail implementation mode and the specific operation process are given, but the scope of protection of the present disclosure is not limited to the following embodiments.

Unless otherwise specified, methods and reagents used in the following embodiments are all conventional methods and conventional reagents.

Single strand oligodeoxynucleotides (ssODN) are purchased from Shanghai Sangon Biotechnology Co. Ltd. and purified through high-performance liquid chromatography. The ssODN used in the present disclosure are listed as follows:

Intact ricin with purity exceeding 95% by a SDS-PAGE test is extracted from castor beans according to the following standard procedure (Tang, J.; Xie, J.; Shao, N.; Yan, Y. Electrophoresis, 2006, 27, 1303-1311). The water-soluble core-shell QDs (the ZnS-capped CdSe QDs, modified with thioglycolic acid) are purchased from Wuhan Jayuan Quantum Dots Co. Ltd. Ricin beta monoclonal antibodies (mAb$_{ricin}$) CP37 and CP75 are purchased from Thermo Scientific. Bis(p-sulfonatophenyl)phenyl phosphine dehydrate dipotassium salt (BSPP) is purchased from the Sigma-Aldrich. Deionized water is purified by a Milli-Q water purification system, and is used throughout this experiment. Sulfo-NHS is purchased from Thermo Scientific.

Instruments used in the present disclosure are as shown below:

The morphology of nanoparticles is observed with a transmission electron microscopy (TEM, JEM-2000EX, Japan).

FT-IR spectra are tested by using Bruker Vertex 70.

Powder X-ray diffraction (XRD) patterns use a product of the Rigaku smart lab (Rigaku, Japan) under the test condition of Cu Kα radiation (λ=1.5406 Å).

Zeta potentials and hydrodynamic sizes are measured by Malvern Nanosizer, purchased from Malvern Instruments Ltd., United Kingdom.

Magnetic properties of magnetic beads are measured by a Physical Property Measurement System (PPMS, Cryogenic, 12 Tesla).

The UV-vis absorption spectra use Shimadzu 3600.

The fluorescence spectra are tested by using Shimadzu RF-5301PC.

Embodiment 1 Preparation and Characterization of Ricin Capture Agent Magnetic Beads (MB@P(C-H)-mAb$_{ricin}$)

Synthesis of 3-methacryloylaminoethyl-2-carboxy-ethyl-dimethylammonium betaine (carboxybetaine methacrylamide) (CBMAA)

According to a previously published procedure (Banerjee, I., Pangule, R. C., Kane, R. S., Adv Mater 2011, 23,690-718). In detail, DMAEMA (19.4 g, 114 mmol) was dissolved in 100 mL of anhydrous THF in a round bottom flask under vigorous stirring and cooled to 0° C. Subsequently, β-propiolactone (11.5 g, 160 mmol) was dissolved in 30 mL of anhydrous THF and added dropwise under argon for a period of about 1 h. The reaction was allowed to proceed for 24 h at 4° C. in a refrigerator. The white precipitate was filtered off, washed with anhydrous THF and ether, and dried under high vacuum. The product was confirmed by $^1$H NMR. The synthetic route is as follows:

Synthesis of Propyl-4-(trimethoxysilyl)benzyl sulfocarbonate (carbonotrithioate) (CTA)

Reversible addition fragmentation chain transfer (RAFT) initiator, propyl-4-(trimethoxysilyl) benzyl carbonotrithioate (CTA), was synthesized according to the literature [(Qu, Z., Hu, F., Chen, K., Duan, Z., Gu, H., Xu, H., J. Colloid and Interface Sci. 2013, 398, 82-87)]. In detail, 1-propanethiol (6.6 mmol) was charged into a stirred suspension of K3PO4 (1.02 g, 6.6 mmol) in anhydrous acetone (15 mL), followed by stirring for about half an hour. CS2 (1.1 mL, 18 mmol) was added and the solution turned to bright yellow. After stirring for another 10 min, (4-(chloromethyl)phenyl)-trimethoxysilane (1.43 mL, 6.6 mmol) was added and the mixture was then stirred at ambient temperature in nitrogen atmosphere for 13 h. The mixture was concentrated, diluted with dichloromethane and filtered off. After removing the solvent from the filtrate under reduced pressure the resulting yellow residue was purified by column chromatography on silica gel to yield a bright yellow oil. The product was confirmed by $^1$HNMR.

Preparation of Magnetic beads MB@P(C-H)

Copolymer brush grafted MBs (MB@P(C-H)) were obtained by RAFT polymerization. In order to obtain $Fe_3O_4$@$SiO_2$ (MBs) modified by an initiator CTA, 50 mg of CTA was added into 100 mL of 1.0 mg/mL magnetic bead absolute ethyl alcohol suspension, and reflux was carried out for 5 hours under the nitrogen. The obtained CTA-MB was collected and washed for three times with ethyl alcohol. Finally, the CTA-MB was suspended in ethyl alcohol for standby application.

In order to obtain a copolymer of the CBMAA and HEMA, i.e., P(C-H) polymer brushes, so as to graft the polymer brushes onto the magnetic beads (MBs), 0.1 g of the standby CTA-MB, 20 mg of AIBN, 1.0 mL of HEMA and 0.3 g of CBMAA were dissolved in 10 mL of degassed water and methyl alcohol mixed solvent (1:1 (v/v)). After bubbling was carried out for 30 minutes with nitrogen, a reaction container was sealed and heated at the temperature of 80° C. After the reaction was performed for 5 hours, a product was diluted and washed for three times with DMF to obtain the MB@P(C-H).

Figure 4A:
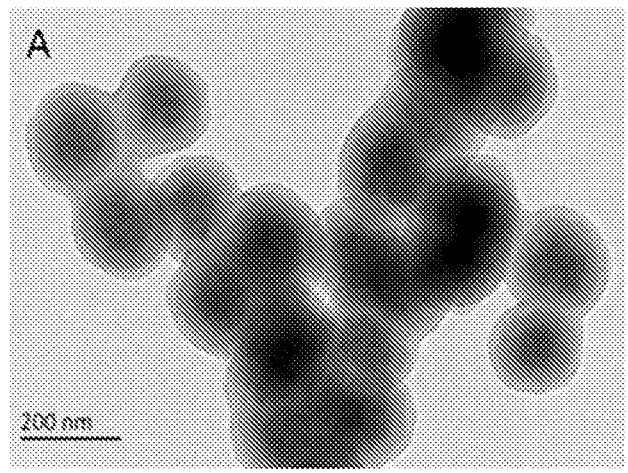
FIGS. 4A and 4B are transmission electron microscopy (TEM) diagrams of MB@P(C-H).
Figure 4B:
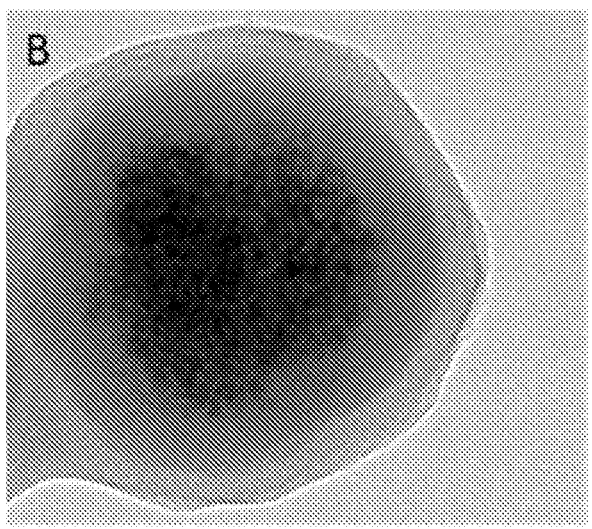

FIG. 4A is a transmission electron microscopy (TEM) diagram of MB@P(C-H), and FIG. 4B is a partial enlarged view. It can be distinguished that the diameter of $Fe_3O_4$ core is about 120 nm, and the $SiO_2$ layer of about 10 nm, polymer brushes P(C-H) of 15-20 nm in thickness, respectively. As measured by DLS, the average hydrodynamic diameter of the MB@P(C-H) was 182 nm with the DPI of 0.24. It was consistent with TEM images.

Figure 5:
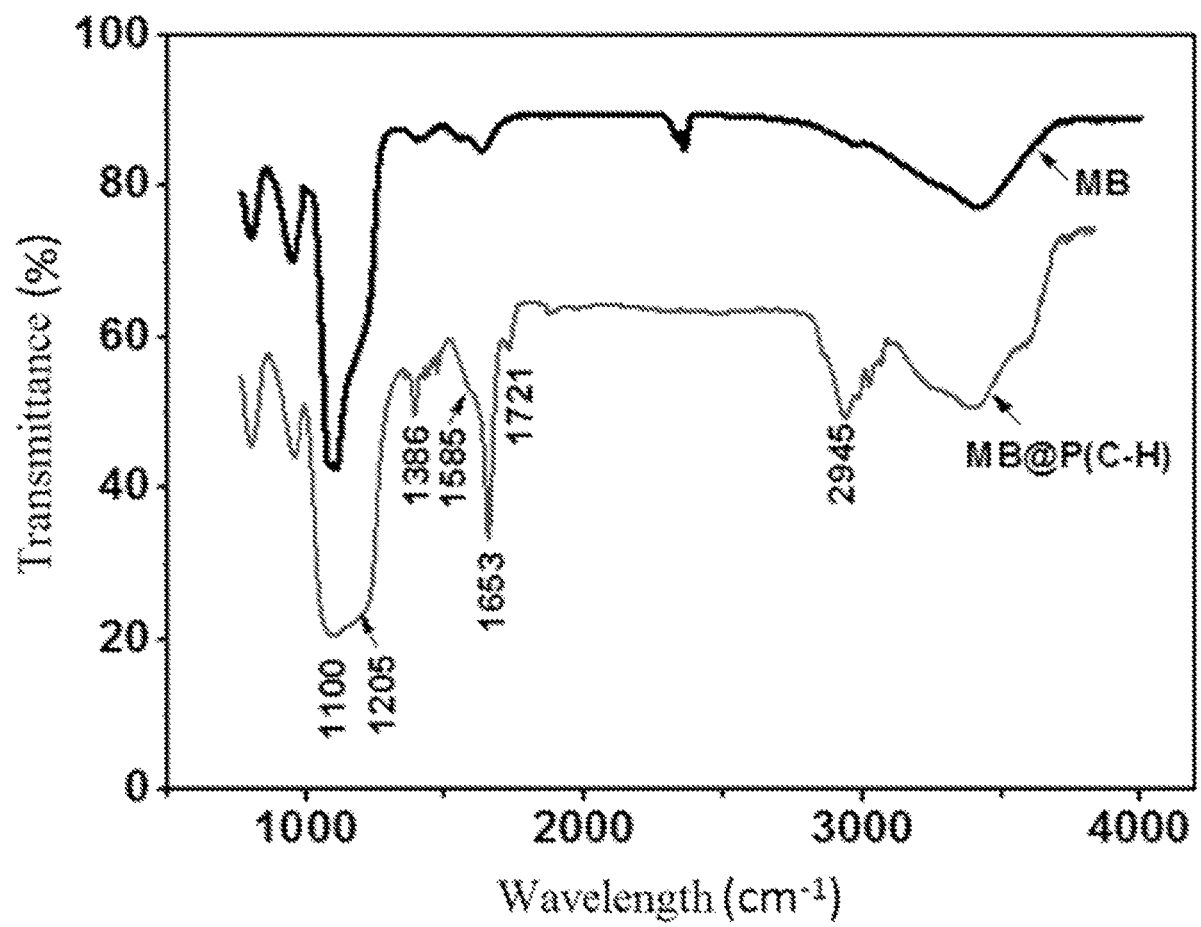
FIG. 5 is an infrared spectrogram obtained by Fourier Transformation Infrared (FT-IR) spectrometry before and after P(C-H) modifies MB.
Figure 6:
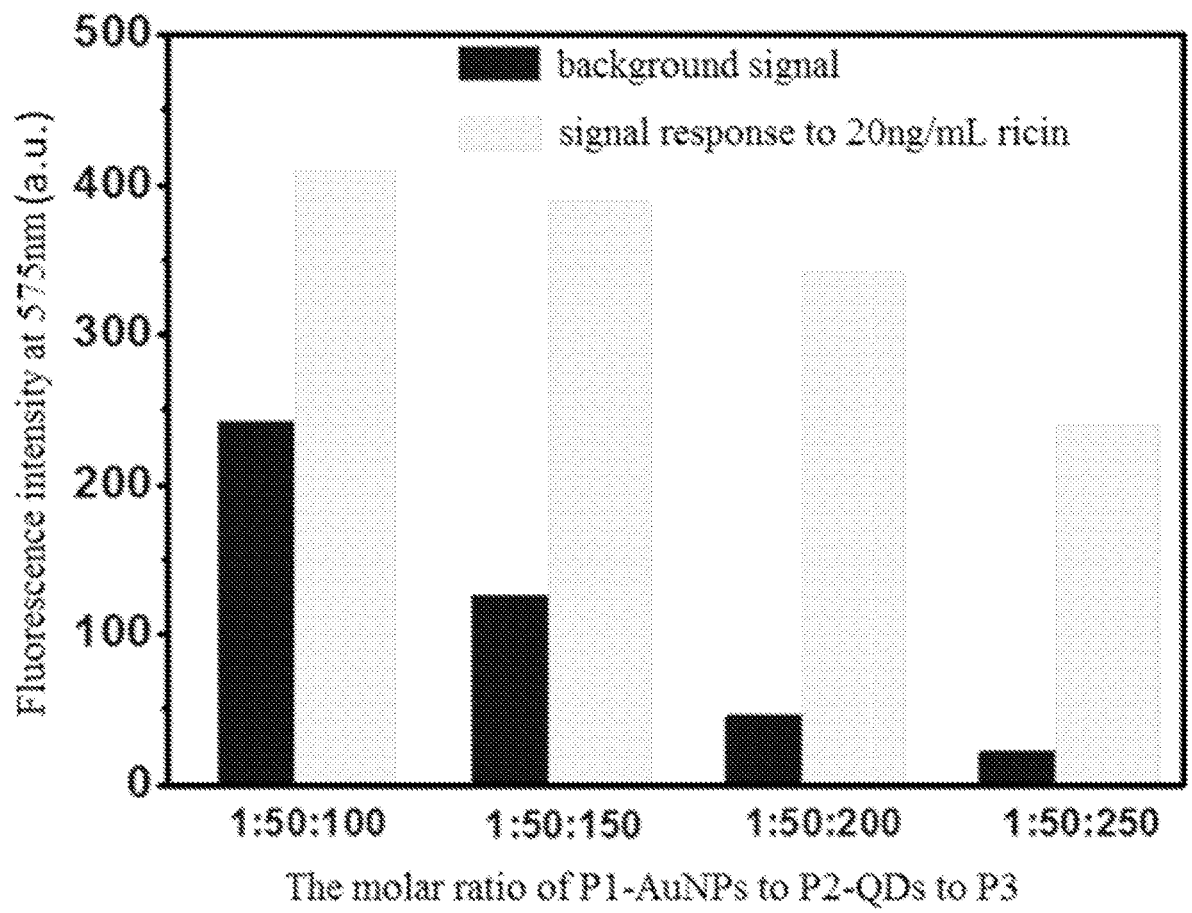
FIG. 6 is comparison of fluorescence intensity background signals and signal response to ricin at different molar ratios of P1-AuPNs to P2-QDs to P3.
Figure 7A:
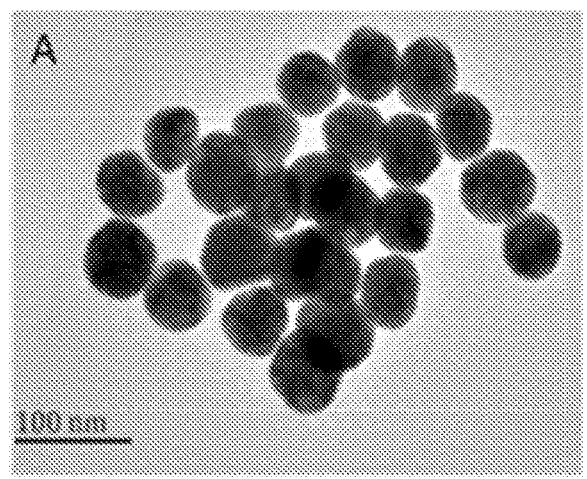
FIGS. 7A-7C show transmission electron microscopy (TEM) diagrams of P1-AuPNs, P2-QDs and an AuPNs/QDs nanoprobe.
Figure 7B:
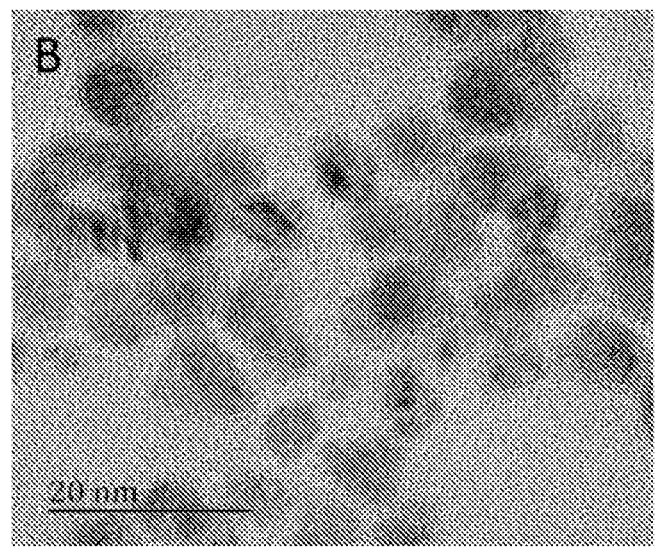
Figure 7C:
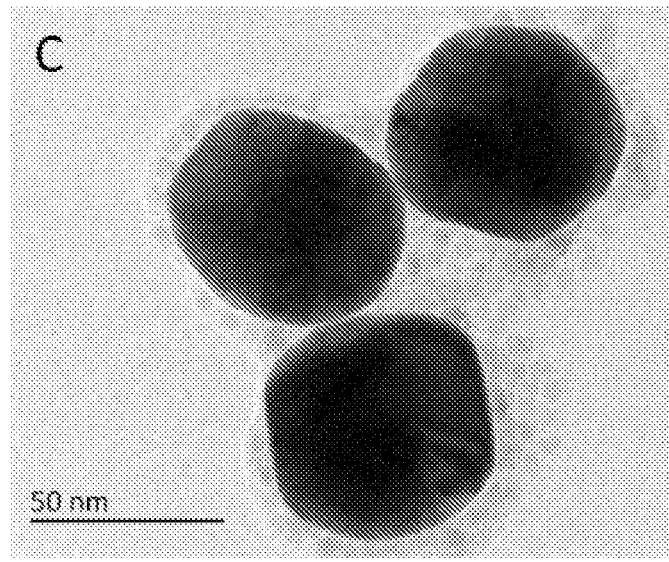
Figure 8:
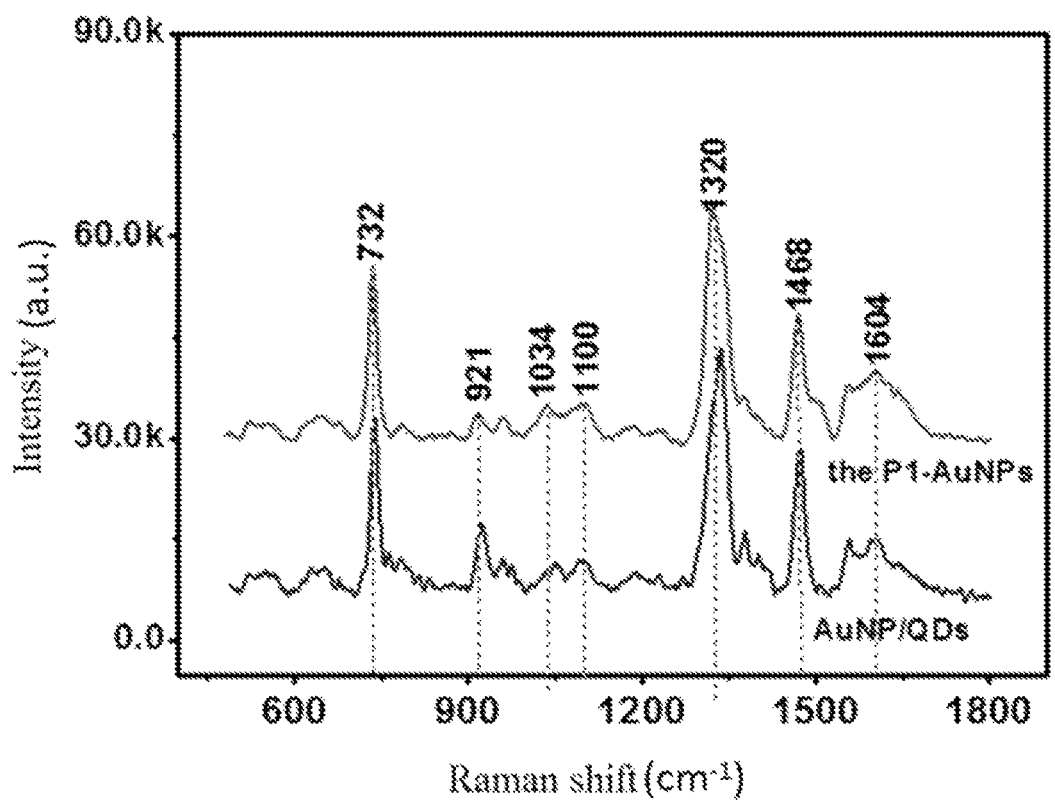
FIG. 8 is a surface-enhanced Raman spectrum of P1-AuPNs and AuPNs/QDs.
Figure 9:
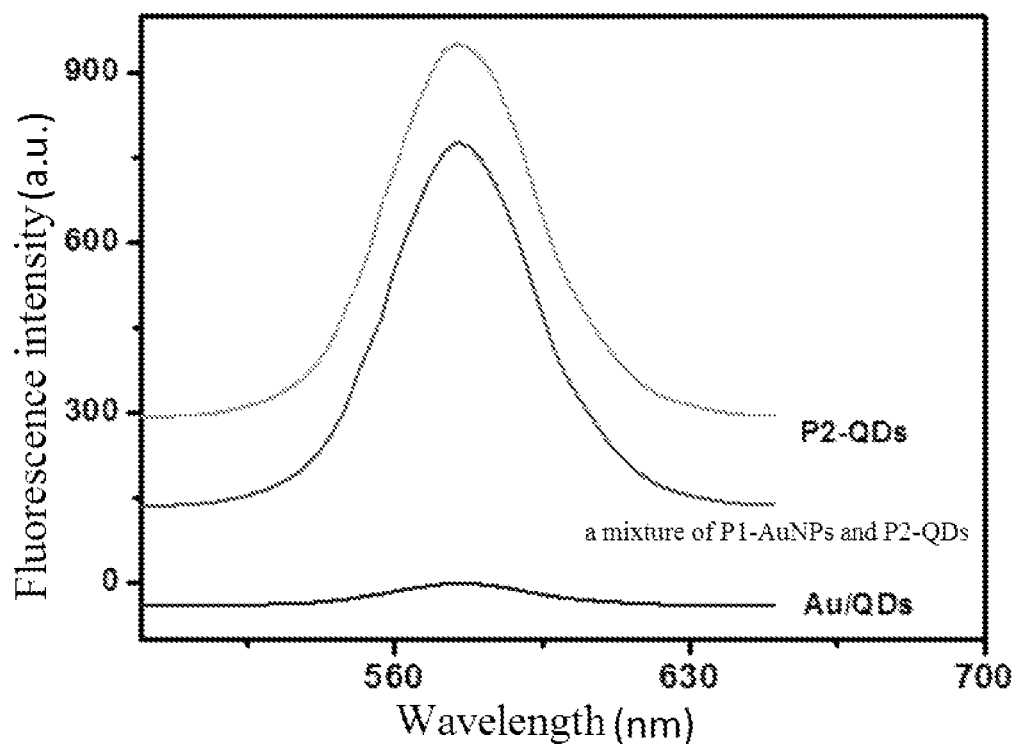
FIG. 9 is a fluorescence spectrum of P2-QDs, a mixture of P1-AuPNs and the P2-QDs, and AuPNs/QDs.
Figure 10A:
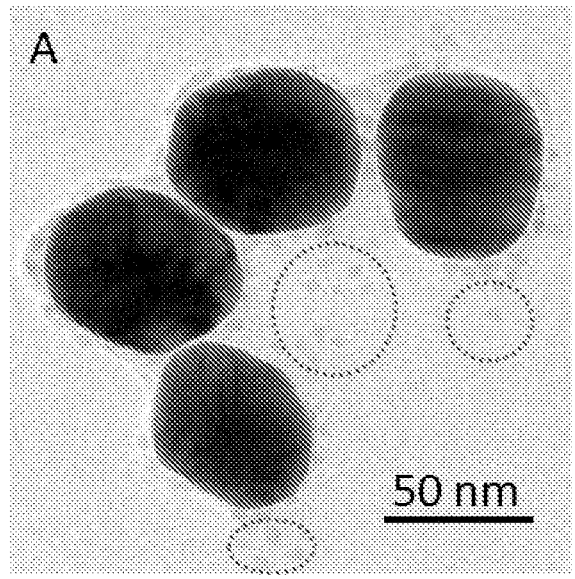
FIGS. 10A and 10B are TEM diagrams 20 min after different concentration of ricin is added into AuPNs/QDs.
Figure 10B:
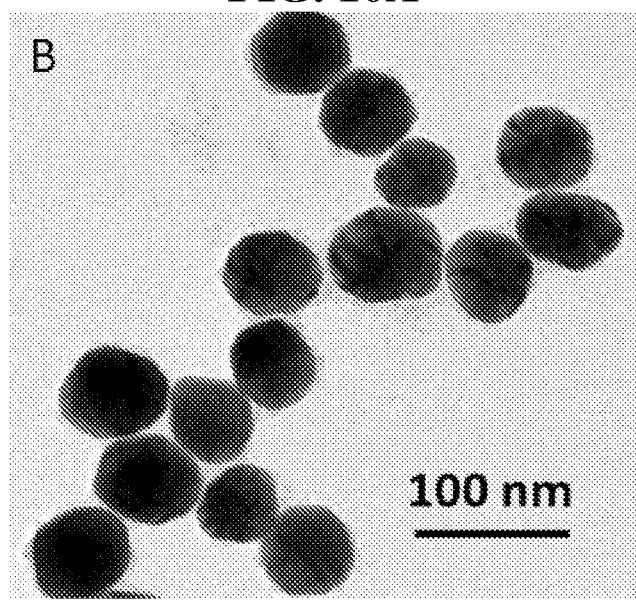
Figure 11:
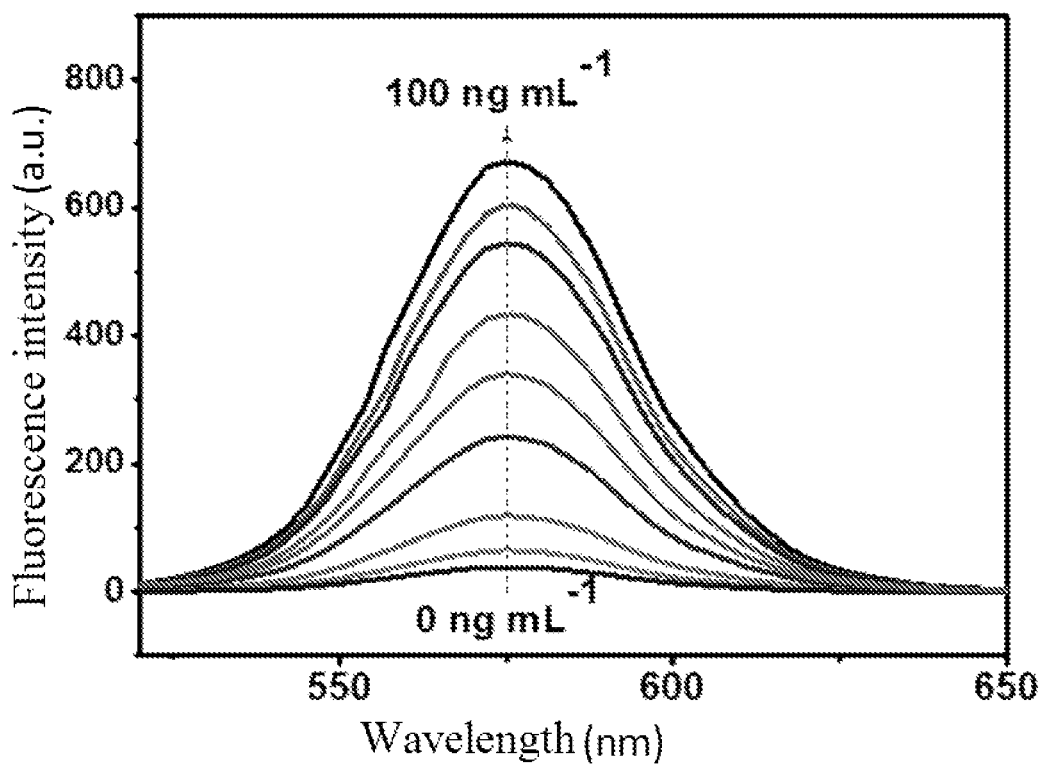
FIG. 11 is a fluorescence spectrum of an AuPNs/QDs nanoprobe buffer solution after active ricin with different concentrations (0 to 100 ng/mL) is added.
Figure 12:
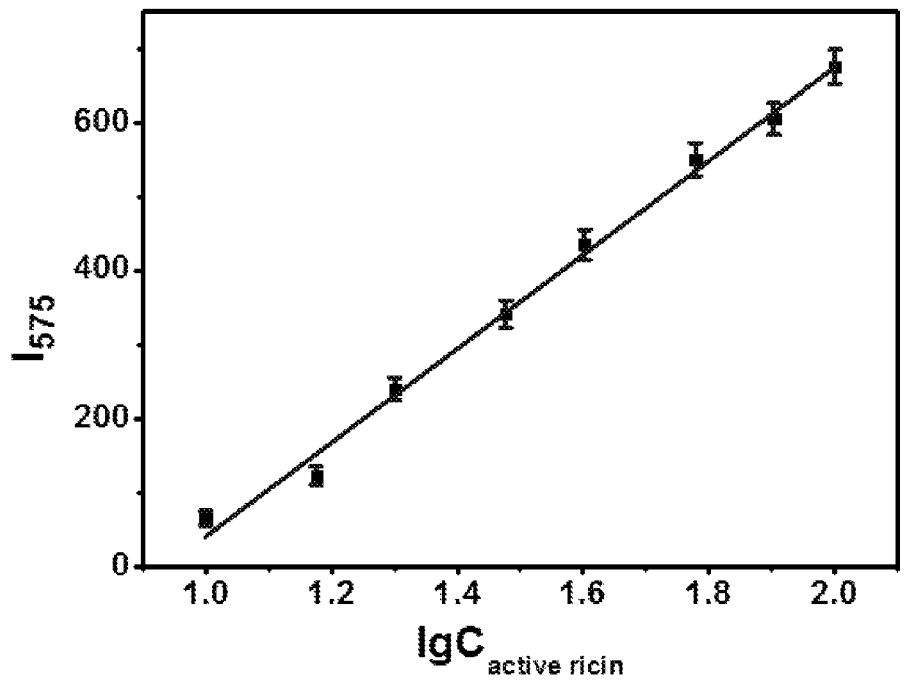
FIG. 12 is a relationship diagram of a denary logarithm value of the concentration (ng/mL) of active ricin and fluorescence intensity of a characteristic peak of AuPNs/QDs at 575 nm.
Figure 13:
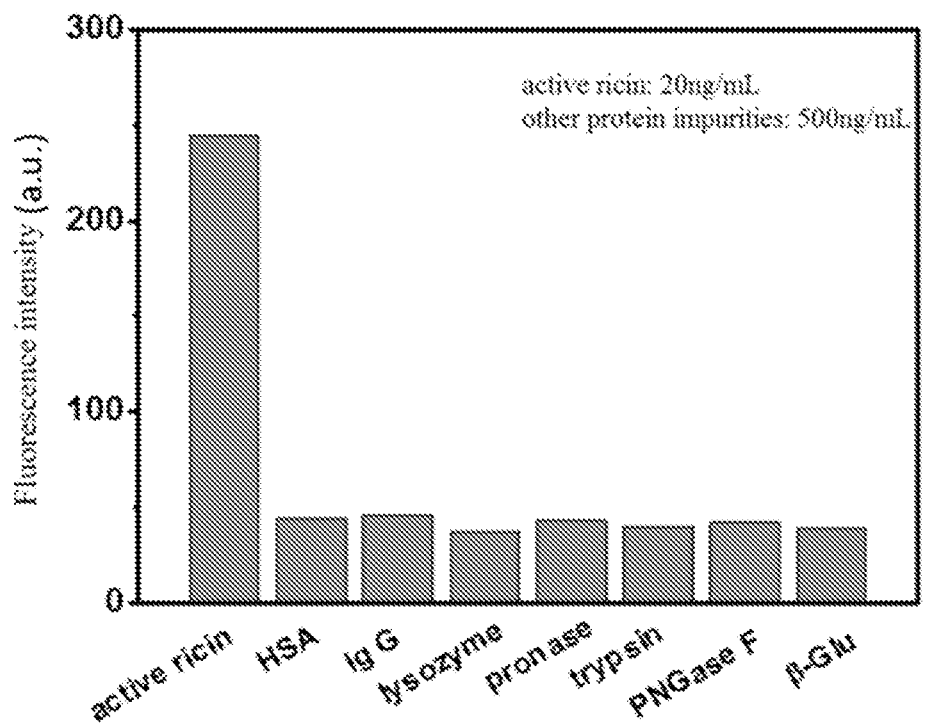
FIG. 13 is a comparison diagram of fluorescence intensity at 575 nm two hours after 20 ng/mL of active ricin and 500 ng/mL of interfering substances are added into an AuPNs/QDs nanoprobe solution.
Figure 14:
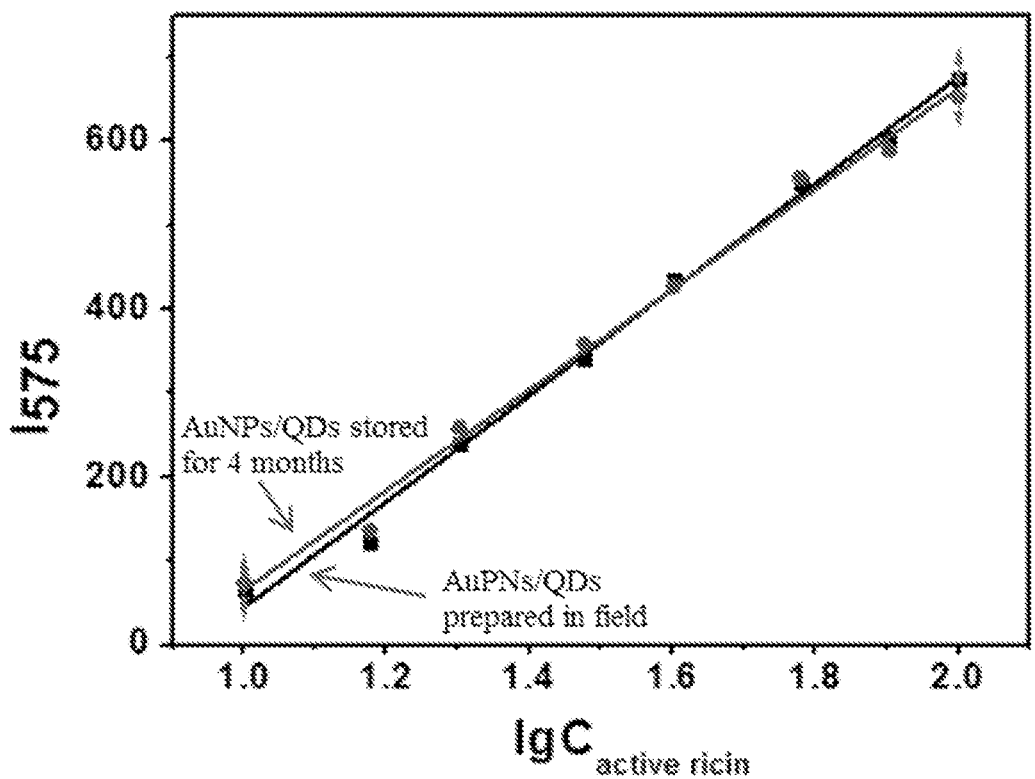
FIG. 14 is a comparison diagram of detection on active ricin by an AuPNs/QDs nanoprobe stored for 4 months and an AuPNs/QDs nanoprobe prepared in field.

In order to further verify that the polymer brushes P(C-H) were really grafted onto the magnetic beads, FIG. 5 is an infrared spectrogram obtained by Fourier Transformation Infrared (FT-IR) spectrometry before and after P(C-H) modifies MB, and it can be seen from the figure that the MB@P(C-H) and the P(C-H) have similar FT-IR spectra. There are strong peaks around 1100 $cm^{-1}$ assigned to Si—O bond which confirm the presence of $SiO_2$ both in the MBs and the MB@P(C-H). As for the MB@P(C-H), the wide absorption band around 3405 $cm^{-1}$ was attributed to the stretching vibration of —OH. Several bands around 2940-2990 $cm^{-1}$ indicate the presence of the alkane groups. The amide bands locate at about 1653 and 1585 $cm^{-1}$. The carboxyl stretching vibration of the —COOH appear at 1721 $cm^{-1}$. In addition, the peak at 1386 $cm^{-1}$ represent the C—O symmetric stretching band. All of these bands indicated the success graft of the P(C-H) on the MBs. It is shown that the MB@P(C-H) has a weight loss of 17% by TGA analysis, which is significantly higher than that of the MBs with less than the 3% weight loss. Moreover, the saturation magnetization of the MB@P(C-H) was measured as 34.5 emu $g^{-1}$, and the magnetization curve exhibits symmetry and passes accurately through the origin, which ensure a facile separation and reusability of the MB@P(C-H) from sample matrices.

Preparation of Ricin Capture Agent Magnetic Beads (MB@P(C-H)-mAb$_{ricin}$)

The ricin capture agent magnetic beads (MB@P(C-H)-mAb$_{ricin}$) were obtained by covalently linking a ricin monoclonal antibody (mAb$_{ricin}$) and the MB@P(C-H). The ricin monoclonal antibody (mAb$_{ricin}$) was covalently linked on the MB@P(C-H) via a typical EDC catalyzed amino-carboxyl coupling reaction. The specific steps were that: the MB@P(C-H) was firstly activated by N-hydroxysulfosuccinimide sodium salt (sulfo-NHS) (10 mg/mL) and EDC (20 mg/mL) in 1.0 mL of 10 mM 2-(N-morpholine)ethanesulfonic acid (MES) buffer; after 30 minutes, a supernatant was removed; 10 mg of mAb$_{ricin}$ (CP37 or CP75) dispersed in a 10 mM PBS solution was added; and the reaction was performed at room temperature for 5 hours, and then the obtained product was allowed to stand overnight at the temperature of 4° C. to obtain the MB@P(C-H)-mAb$_{ricin}$ after the reaction was quenched by 0.5% glycine.

Embodiment 2 Capture Ability of Ricin Capture Agent Magnetic Beads (MB@P(C-H)-mAb$_{ricin}$) for Ricin For extracting ricin, a series of standard solutions with the ricin concentrations ranged from 10 to 50 μg/mL was added to 1.0 mL, 50 mg/mL of ricin capture agent magnetic beads (MB@P(C-H)-mAb$_{ricin}$) solution. After incubating 2 h, the equilibrium concentrations of ricin in the supernatants were determined by the BCA protein assay. In addition, the binding kinetic between ricin and the MB@P(C-H)-mAb$_{ricin}$ was examined by mixing 50 mg of the MB@P(C-H)-mAb$_{ricin}$ with 50 μg ricin in 1.0 mL PBS buffer. At different incubating times from 20 to 120 min, the concentrations of ricin in the supernatant were determined by the BCA protein assay. The equilibrium adsorption amount (Q) of the MB@P(C-H)-mAb$_{ricin}$ was calculated based on the equation below:

$$Q=(C_0-C_e) \cdot V \cdot m^{-1} \cdot 10^3 (mg/g).$$

Here, $C_0$ (μg $mL^{-1}$) represent the initial ricin concentration in PBS buffer; $C_e$ (μg $mL^{-1}$) is the equilibrium concentration of ricin in the supernatant; V (mL) is the volume of sample solution; m (g) is the mass of the MB@P(C-H)-mAb$_{ricin}$.

It is found that each gram of the MB@P(C-H))-mAb$_{ricin}$ contained 28 mg monoclonal antibody mAb$_{ricin}$, and each gram of the MBs contained 6.2 mg monoclonal antibody mAb$_{ricin}$. It is demonstrated that polymer brushes P(C-H) have influence on magnetic beads capture agent. The MB@P(C-H)-mAb$_{ricin}$ reached to the saturated adsorption within 20 min, suggesting the flexible interface of the MB@P(C-H)-mAb$_{ricin}$ facilitated the recognition and binding between mAb$_{ricin}$ and ricin by decreasing steric hindrance, thus achieved fast adsorption balance. In order to achieve the full recovery rate, in the embodiment of the present disclosure, the time of capturing ricin by the MB@P(C-H)-mAb$_{ricin}$ was 1 h. Table 2 is a comparison of the active ricin capture abilities when two types of different magnetic beads, i.e., the MB@P(C-H)-Ab$_{ricin}$ prepared in the present disclosure and MB@P(ConA/Gal) previously prepared by the inventor (refer to the document Anal. Chem.

2017, 89, 12209-12216), were used as capture agents in complex matrices. Concentration of active ricin was tested by LC-MS/MS.

TABLE 2

| Sample | Concentration of added ricin (ng/mL) | Concentration of ricin captured by MB@P(C-H)-mAb$_{ricin}$ (ng/mL) | Concentration of ricin captured by MB@P(ConA/Gal) (ng/mL) |
| --- | --- | --- | --- |
| Diluted Human Serum | 5.0 | 4.1 | 2.1 |
| | 50.0 | 43.0 | 28.3 |
| Orange Juice | 5.0 | 4.2 | 2.5 |
| | 50.0 | 44.5 | 32.5 |
| Ham | 5.0 | 3.6 | 1.7 |
| | 50.0 | 39.3 | 19.8 |
| Sandwich | 5.0 | 3.7 | 1.2 |
| | 50.0 | 38.5 | 21.6 |
| Milk | 5.0 | 4.1 | 1.5 |
| | 50.0 | 42.3 | 24.3 |
| Coffee | 5.0 | 4.3 | 3.2 |
| | 50.0 | 45.6 | 37.6 |

It can be seen from Table 2 that the capture agent MB@P(C-H)-mAb$_{ricin}$ provided by the present disclosure can efficiently capture the ricin in various complex and polluted matrices, the concentration of the ricin was measured by LC-MS/MS, and the recovery rate can achieve 72.0% to 86.0% (5 ng/mL) and 77.0% to 92% (50 ng/mL). Compared with the MB@P(ConA/Gal), the capture agent MB@P(C-H)-mAb$_{ricin}$ of the present disclosure also has good capture ability for the ricin even in the complex matrices due to the double effects of the anti-fouling capacity of the polymer brushes P(C-H) and the introduction of the ricin monoclonal antibody mAb$_{ricin}$, thereby achieving the objective of detecting the trace amount of ricin.

Embodiment 3 Assembly and Characterization of Gold/Quantum Dot Nanoprobe (AuNPs/QDs)

Single strand oligodeoxynucleotides (ssODN) used in this embodiment were P1 (a), P2 (a) and P3 (a) in Table 1, respectively.

Spherical gold nanoparticles (AuNPs) were obtained by a seed growth method, the method can refer to the document (Bastús, N. G., Comenge, J., Puntes, V., Langmuir 2011, 27, 11098-11105), and the diameter was about 60 nm. After six times of growth, the concentration of AuNPs gel was $1.9\times10^{11}$ (NP/mL). For stabilizing the gold nanoparticles, 15 mg of BSPP was added to 100 mL of gold nanoparticle sol under stirring and then a reaction was conducted for at least 10 hours. The obtained BSPP-AuNP sol was centrifuged, a supernatant was removed and then the obtained product was dispersed into 10 mL of ultrapure water. P1 modified gold nanoparticles (P1-AuNPs) were obtained via strong binding between gold particles and thiol, and the specific steps were that: 50 μL of 0.1 mmol/L P1 (a) was treated with tris(2-carboxyethyl)phosphine hydrochloride (TCEP) of which the molar weight is 5 times of that of the P1 (a) for 1 hour at the temperature of 50° C. to reduce disulfide bonds, and then the treated P1 (a) was added into the BSPP-AuNP sol. In the incubation process, 0.1 mL of 0.1 mol/L NaCl solution was added every two hours. After 10 hours, P1 (a)-AuNPs were centrifuged at 8000 rpm for 10 minutes, and the supernatant was carefully removed.

P2 modified quantum dots (P2-QDs) were prepared by using an EDC/sulfo-NHS cross-linking method, and the specific steps were that: firstly, commercially purchased quantum dots were purified by utilizing a hyperconcentration technology, and then the purified quantum dots were diluted to 1.0 μM with ultrapure water; the quantum dots were activated by sulfo-NHS (0.1 mg $mL^{-1}$) and EDC (0.1 mg $mL^{-1}$) in 1.0 mL of 1.0 mM MES buffer; after the reaction was performed for 30 minutes, P2 (a) (0.1 mmol/L, 100 μL) was added into the activated quantum dot solution, and 0.1M $NaHCO_3$ was added to regulate pH to 8.5; the reaction was continued to be carried out for 10 hours at room temperature, the reaction was quenched by 0.5% glycine, and the obtained product was kept overnight at the temperature of 4° C.; and P2 (a)-QDs were purified by dextrangel-G50.

Assembly of the AuNP/QDs nanoprobe was carried out in a buffer solution, and the buffer solution included 10 mM PBS with a pH of 7.4, 5 mM $MgCl_2$ and 0.01% Tween 20. Generally, the P1 (a)-AuNPs, the P2 (a)-QDs and P3 (a) were mixed in a molar ratio of 1:50:200. The pairing hybridization reaction of bases was performed for 10 minutes at the temperature of 80° C., and then was performed for 2 hours at the temperature of 37° C. so as to obtain a fluorescence quenched AuNP/QD nanostructure probe. The AuNP/QD nanoprobe was subjected to centrifugal separation and purification, and was suspended in a 10 mM PBS buffer solution for later use.

Fluorescence intensity background signals and signal response to ricin at different molar ratios of the P1-AuPNs to the P2-QDs to the P3 were tested, the molar ratios of the P1-AuPNs to the P2-QDs to the P3 were 1:50:100, 1:50:150, 1:50:200 and 1:50:250, respectively, detection results were shown in FIG. 6, and in comprehensive consideration of the detection sensitivity and the signal-to-noise ratio, the molar ratio of the P1-AuPNs to the P2-QDs to the P3 was 1:50:200.

The prepared AuNPs/QDs nanoprobe was subjected to characterization. FIGS. 7A and 7B show transmission electron microscopy (TEM) diagrams of P1-AuPNs, P2-QDs and an AuPNs/QDs nanoprobe. FIG. 7A is a TEM diagram of the P1-AuPNs, and shows a spherical structure with the diameter of about 60 nm. The Zeta potential and the hydrodynamic diameter of the AuNPs unmodified by the P1 were −17.8 mV and 63 nm, respectively, and the Zeta potential and the hydrodynamic diameter of the P1 modified AuNPs were −26.5 mV and 68 nm, respectively. FIG. 7B is a TEM diagram of the P2-QDs, and shows a spherical structure with the average diameter of 6 nm. The Zeta potential and the hydrodynamic diameter of the QDs unmodified by the P2 were −23.7 mV and 10 nm, respectively, and the Zeta potential and the hydrodynamic diameter of the P2 modified QDs were −25.4 mV and 14 nm, respectively. The zeta potential of the AuNPs/QDs was −24.6 mV, while the hydrodynamic diameter was increased to 96.3 nm. FIG. 7C is a TEM diagram of a core-satellite structure of the AuNPs/QDs, and it can be seen from the figure that the bases on the single strand oligodeoxynucleotides (ssODN) P1, P2 and P3 were subjected to pairing hybridization to form double strand oligodeoxynucleotides (dsODN) so as to assemble the AuNPs and the QDs into the core-satellite structure. FIG. 8 is a surface-enhanced Raman spectrum of P1-AuPNs and AuPNs/QDs, a peak at 1,037 $cm^{-1}$ showed wagging adsorption of a C—N bond, a peak at 1,320 $cm^{-1}$ showed stretching adsorption of the C—N bond, a peak at 1,468 $cm^{-1}$ showed stretching of $COO^-$, and existence of the SERS peak above showed existence of the single strand oligodeoxynucleotides. FIG. 9 is a fluorescence spectrum of P2-QDs, a mixture of P1-AuPNs and the P2-QDs, and AuPNs/QDs. It can be obviously seen from the figure that after the QDs and the AuPNs formed the core-satellite structure through forming the double strand linkers, the distance between the QDs and the AuPNs was sufficiently small, and thus, a fluorescence quenching phenomenon was generated, so that the fluorescence characteristic peak of the AuNPs/QDs at 575 nm basically disappeared. An ideal energy receptor/donor was formed between the AuNPs and the QDs through fluorescence resonance energy transfer (FRET) so as to effectively quench fluorescence of the QDs. The phenomena all showed that the double strand structure was formed by pairing hybridization of the single strand oligodeoxynucleotides (ssODN) P1, P2 and P3 and the core-satellite structure of the AuNPs/QDs was assembled.

Embodiment 4 Detection on Active Ricin by Using AuNPs/QDs Nanoprobe

An AuNP/QD nanoprobe (0.5 OD) reacted with active ricin with various concentrations (0, 10, 15, 20, 30, 40, 60, 80 and 100 ng/mL) in an ammonium acetate buffer solution (200 μL, 5 mmol/L, pH 4.0) in a 96-well plate. Incubation was carried out for 2 hours at the temperature of 38° C., and the fluorescence intensity of the solutions was tested. In order to monitor depurination reaction dynamics between the active ricin and the AuNP/QD nanoprobe (0.5 OD), the fluorescence values of the solutions were detected every 20 minutes, until the fluorescence intensity was stable.

FIG. 10A is a TEM diagram after 30 ng/mL of active ricin is added into an AuNPs/QDs nanoprobe buffer solution, FIG. 10B is a TEM diagram after 80 ng/mL of active ricin is added into the AuNPs/QDs nanoprobe buffer solution, and particles in the circles in the figures were dissociated QDs. FIGS. 10A and 10B showed that when the concentration of the active ricin was gradually increased, more and more QDs were dissociated from AuNPs, so that the QDs were not quenched due to the fact that the QDs were away from the AuNPs. In consideration of the relationship between the specific depurination reaction of the active ricin and the reaction time as well as the concentration of the active ricin, in the monitoring process, 2 h was selected to be used as the reaction time, and then the fluorescence intensity was only related to the concentration of the ricin.

FIG. 11 is a fluorescence spectrum of an AuPNs/QDs nanoprobe buffer solution after active ricin with different concentrations (0, 10, 15, 20, 30, 40, 60, 80 and 100 ng/mL) is added. It can be seen from the figure that the concentration of the added active ricin was gradually increased, and the fluorescence intensity of the characteristic peak of the AuNPs/QDs at 575 nm was gradually reduced. FIG. 12 is a relationship diagram of a denary logarithm value of the concentration of the active ricin and the fluorescence intensity of a characteristic peak of AuPNs/QDs at 575 nm, and a diagram of a Langmuir type is obtained. When the concentration of the active ricin exceeded 100 ng/mL, the curve showed nonlinearity, and probably because adsorption of the probe achieved a saturated state under higher concentration of the active ricin; and when the concentration of the active ricin was within a range of 10 to 100 ng/mL, the curve showed a good linear relationship. By the curve, the following formula can be obtained:

$$I_{575}=634.8\cdot lgC-594.7(R^2=0.995)$$

Wherein $I_{575}$ represents the fluorescence intensity of the characteristic peak of the AuNPs/QDs at 575 nm, C represents the concentration of the active ricin, and the unit is ng/mL. Therefore, the fluorescence intensity of a sample was detected, and then the concentration of the active ricin in the sample can be calculated by the formula above. The limit of detection obtained by the method was 7.46 ng/mL, and the value was calculated by a control signal with three times of a standard deviation. A relative standard deviation (RSD) of 6 times of parallel detection on 50 ng/mL of ricin was 5.4%, showing that the detection method of the present disclosure has very good repeatability.

In order to detect anti-interference performance of the method of the present disclosure, the intensity of the fluorescence characteristic peak of the AuNPs/QDs at 575 nm in each interfering substance was tested. FIG. 13 is a comparison diagram of the fluorescence intensity at 575 nm two hours after 20 ng/mL of active ricin and 500 ng/mL of interfering substances are added into the AuPNs/QDs nanoprobe solution. It can be seen that common organic matters cannot generate a fluorescence switch-on effect on the AuNPs/QDs even under the high concentration (500 ng/mL), while the active ricin can generate a strong switch-on effect on the AuNPs/QDs nanoprobe provided by the present disclosure under the concentration of 20 ng/mL, so that the fluorescence intensity of the AuNPs/QDs at 575 nm was obviously improved and a very excellent anti-interference capacity was showed.

Whether the ricin exists in the sample can also be qualitatively judged by judging whether the fluorescence is switched on. For example, the AuNPs/QDs nanoprobe provided by the present disclosure is added into the to-be-detected sample, after the sample is stabilized for a period of time, the sample is irradiated with an ultraviolet light flashlight in a dark place, and if the sample solution emits orange light, it is indicated that the active ricin with a certain concentration exists in the sample. That is because that if the active ricin exists in the sample, after the AuNPs/QDs nanoprobe is added, the fluorescence of the QDs can be switched on again, and at the moment, if the sample is irradiated with ultraviolet light, a photoluminescence phenomenon is generated, and light visible to naked eyes is generated. In addition, the AuNPs/QDs nanoprobe provided by the present disclosure has very high anti-interference capacity, and common organic impurities with high concentration also cannot generate a switch-on effect on the AuNPs/QDs nanoprobe. Therefore, by means of the AuNP/QD nanoprobe provided by the present disclosure, an effect of rapidly and visually detecting whether the ricin exists in the sample in field can be achieved only through the ultraviolet light flashlight without the help of other equipment.

Embodiment 5 Selective Detection on Ricin in Various Complex Matrices

Preparation of Sample

Various complex food and biological samples were used for detection so as to evaluate reliability of the detection method. The samples included lettuces, chicken, bread, fresh milk, coffee and human plasma. Coarse food and biological samples of the present disclosure were respectively prepared from diluted human serum, orange juice, coffee, fresh milk and sandwiches. A specific method included the steps: weighing a solid sample and diluting the solid sample with a PBS buffer solution, a volume-mass ratio of the PBS buffer solution to the solid sample being 1.0 mL/g; and after homogenizing for 5 min, centrifuging for 2 minutes at 1,200 rpm so as to remove large-volume residues. The human serum is diluted with the PBS buffer solution by 5 times. All the samples were filled with ricin with the specific concentration.

Enrichment of Ricin 5 mg of MB@P(C-H)-mAb$_{ricin}$ and 1.0 mL of the sample solution containing the ricin were directly added into a test tube, and were continuously stirred and mixed for 1 hour. By adsorption of a magnet for magnetic beads, the magnetic beads capturing the ricin were enriched at the bottom of the test tube, a supernatant was poured out, the magnetic beads were eluted for 30 minutes with 100 μL of trifluoroacetic acid (TFA)/deionized water/ethyl alcohol (1:50:49, v/v/v) eluent at the temperature of 25° C. after being washed with PBST and PBS buffer solutions, then 0.9 mL of ammonium acetate buffer solution (5 mmol/L, pH 4.0) was added, and the ricin captured by the magnetic beads was released again.

Detection of Ricin

The ricin in the samples was detected by the AuNP/QD nanoprobe according to the method in Embodiment 4. In order to verify reliability of detection of active ricin by the AuNP/QD nanoprobe provided by the present disclosure, the ricin was also measured by LC-MS/MS as comparison. Detection results were shown as Table 3.

TABLE 3

| Samples | Concentration of added ricin (ng/mL) | AuNPs/QDs nanoprobe method: Monitoring concentration (ng/mL) | AuNPs/QDs nanoprobe method: Recovery rate (%) | LC-MS/MS method (ng/mL) |
|---|---|---|---|---|
| Diluted Human Serum | 50.0 | 38.4 | 76.8 | 43.0 |
| Orange Juice | 50.0 | 39.5 | 79.0 | 44.5 |
| Ham | 50.0 | 34.3 | 68.6 | 39.3 |
| Sandwich | 50.0 | 32.7 | 65.4 | 38.5 |
| Milk | 50.0 | 37.3 | 74.6 | 42.3 |
| Coffee | 50.0 | 39.6 | 79.2 | 45.2 |

It can be seen from Table 3 that the AuNPs/QDs nanoprobe provided by the disclosure shows excellent accuracy and sensitivity when used for detection on the active ricin. The method based on the AuNPs/QDs nanoprobe provided by the present disclosure and the LC-MS/MS method obtain the basically consistent results, which shows reliability of the detection method provided by the present disclosure. A lethal dose LD50 of taking in the ricin is estimated as 3 mg/kg, and for a child with a weight of 35 kg, a lethal dose of taking in the ricin is 105 mg. By taking a beverage as an example, the lethal oral intake ricin concentration is about 0.4 mg/mL, and the limit of detection of the detection method using the AuNPs/QDs nanoprobe provided by the present disclosure is much less than the human body intake lethal dose in a general case. In the high-concentration active ricin sample, quantitative and semi-quantitative detection of the concentration of the active ricin can be carried out only by testing the fluorescence intensity at 575 nm after the AuNPs/QDs nanoprobe is added into the sample. In case that there is no need to clearly know the concentration of the ricin, just in the qualitative judgment of whether the ricin exists, the present disclosure provides a simpler method, i.e., a treated sample solution is added into an AuNPs/QDs nanoprobe solution, if the active ricin exists in the sample, the specific depurination reaction can be performed, then adenine on an AuNPs/QDs linker can be cut off so as to make the double strand linker loose, then QDs are dissociated from AuNPs, the fluorescence of the QDs is not quenched any more, at the moment, the sample solution is directly irradiated with an ultraviolet light flashlight, and due to photoluminescence, if the ricin exists in the sample, light visible to naked eyes can be emitted. Visual detection without large-sized equipment is implemented.

Embodiment 6 Storage Stability Test of AuNPs/QDs Nanoprobe

In order to further detect whether a prepared AuNPs/QDs nanoprobe still has a detection effect on active ricin after being stored for a period of time, this embodiment was carried out. After the AuNPs/QDs nanoprobe was stored in a PBS buffer solution at the temperature of 4° C. for 1 month and 4 months, the fluorescence intensity of samples containing different concentrations of active ricin at 575 nm was detected according to the method in Embodiment 4 so as to obtain FIG. 14. After the AuNPs/QDs nanoprobe was stored for 4 months, a linear relationship formula between the concentration C (ng/mL) of the active ricin and the fluorescence intensity at 575 nm was that:

$$I_{575}=628.4\cdot lgC-586.5(R^2=0.993)$$

It can be seen from FIG. 14 that after the AuNPs/QDs nanoprobe was stored for 1 month, the curve basically coincided with that before storage; and after the AuNPs/QDs nanoprobe was stored for 4 months, the curve was slightly deviated, but still can meet the requirement for detection on the active ricin.

Embodiment 7 Comparison of Various Methods for Detecting Active Ricin

Table 4 listed some common methods for detecting active ricin. According to the method provided by the present disclosure, the active ricin was detected by means of the fluorescence quenched and switch-on process of AuNPs/QDs. Concentration of the active ricin can be known only by monitoring the fluorescence intensity of a sample without large-sized equipment. Tests prove that the method provided by the present disclosure is sensitive, reliable and short in time, and does not require large-sized instruments. In addition, in some special occasions, there is no need to know the specific concentration of the ricin, but it only needs to judge whether the ricin exists, and the present disclosure provides a visual method capable of carrying out detection in field, so that whether the ricin exists can be known only by one ultraviolet light flashlight through detecting whether the sample is in the fluorescence switch-on state, and an effective method is provided for rapid naked eye detection on the ricin.

TABLE 4

| Methods | Detection Time | Required Instrument Equipment | Limit of Detection | Samples | Ref. |
|---|---|---|---|---|---|
| Magnetic Bead Enrichment-Fluorescence Method | nearly 4 h | naked eyes or spectrophotometer | 7.46 ng mL$^{-1}$ | diluted human serum, orange juice, ham, sandwich, milk and coffee | the present disclosure |
| Affinity Magnetic Enrichment | nearly 4 h | Naked eyes or ultraviolet- | 12.5 | juice, diluted human serum and | Ref. 1 |

TABLE 4-continued

| Methods | Detection Time | Required Instrument Equipment | Limit of Detection | Samples | Ref. |
| --- | --- | --- | --- | --- | --- |
| and Colorimetric Method | | visible spectrophotometer | ng mL$^{-1}$ | drinking water | |
| Luminescence Analysis | nearly 2 h | spectrophotometer | 0.8 ng mL$^{-1}$ | buffer solution | Ref. 2 |
| Real-Time Mass Spectrometry Detection | nearly 6 h | mass spectrometer | 5.7 μg mL$^{-1}$ | buffer solution | Ref. 3 |
| Immunocapture and Mass Spectrometry Detection | nearly 4 h | mass spectrometer | 0.32 ng mL$^{-1}$ | milk, juice, serum and saliva | Ref. 4 |
| Surface Enhanced Raman Spectrometry | nearly 3 h | Raman spectrometer | 8.9 ng mL$^{-1}$ | juice, diluted human serum and drinking water | Ref. 5 |
| Immunocapture and Matrix-Assisted Laser Desorption Ionization Time-of-Flight Mass Spectrometry | nearly 6 h | matrix-assisted laser desorption ionization time-of-flight mass specrometry | 0.2 ng mL$^{-1}$ | buffer solution and milk | Ref. 6 |

Ref. 1: Sun, J., Wang, C., Shao, B., Wang, Z., Xue, D., Liu, Y., Qi, K., Yang, Y.; Niu, Y. Anal. Chem., 2017, 89, 12209-12216.

Ref. 2: Sturm, M. B., Schramm, V. L., Anal. Chem., 2009, 81, 2847-2853.

Ref. 3: Bevilacqua, V. H., Nilles, J. M., Rice, J. S., Connell, T. R., Schenning, A. M., Reilly, L. M., Durst, H. D., Anal. Chem., 2010, 82, 798-800.

Ref. 4: Kalb, S. R., Barr, J. R., Anal. Chem. 2009, 81, 2037-2042.

Ref. 5: Tang, J., Sun, J., Liu, R., Zhang, Z., Liu, J., Xie, J., ACS Applied Materials & Interfaces, 2016, 8, 2449-2455.

Ref. 6: Wang, D., Baudys, J., Barr, J. R., Kalb, S. R., Anal. Chem., 2016, 88, 6867-6872.

The specific embodiments above merely are used for schematically illustrating the contents of the present disclosure, but not intended to limit the contents of the present disclosure. What those skilled in the art can think of is that the specific structure in the present disclosure can have other change forms.

What is claimed is:

1. A gold/quantum dot nanoprobe for detecting active ricin, comprising gold nanoparticles modified by a linker P1 containing single strand oligodeoxynucleotides (P1-AuNPs), quantum dots modified by a linker P2 containing single strand oligodeoxynucleotides (P2-QDs) and single strand oligodeoxynucleotides P3, wherein:
the P1, the P2 and the P3 form double strand oligodeoxynucleotides by base pairing hybridization, the gold nanoparticles and the quantum dots are linked to be assembled into a core-satellite structure with the gold nanoparticles being a core and the quantum dots surrounding the gold nanoparticle core;

a 5' terminal of the linker P1 is sulfydryl and is linked with the surfaces of gold nanoparticles AuNPs to obtain the P1 modified gold nanoparticles (P1-AuNPs) and a 3' terminal is a deoxynucleotide sequence L1;

a 3' terminal of the linker P2 is amino and is linked with quantum dots QDs to obtain the P2 modified quantum dots (P2-QDs) and a 5' terminal is a deoxynucleotide sequence L2;

the linkers P1 and P2 are respectively subjected to pairing hybridization with deoxynucleotide sequences L1' and L2' at both ends of the P3 to form a double strand structure to link the AuNPs and the QDs;

a condensed structural formula of the linker P1 is 5'-SH-alkylene-poly($dT_{n1}$)-L1-3', a condensed structural formula of the linker P2 is 5'-L2-poly($dT_{n2}$)-alkylene-$NH_2$-3', and a condensed structural formula of the linker P3 is 3'-L1'-poly($dA_{n3}$)-L2'-5', wherein the number of carbon atoms of alkylene is an integer within a range of 4 to 12;

poly($dT_{n1}$) and poly($dT_{n2}$) represent chains of deoxynucleotides of which a base is thymine (T), and n1 and n2 represent numbers of deoxynucleotides of which the base is the thymine (T) and are independently 6 to 15;

poly($dA_{n3}$) represents a sequence of deoxynucleotides of which a base is adenine (A), n3 represents a number of deoxynucleotides of which the base is the adenine (A), and the number is an integer within a range of 9 to 21;

L1 represents a sequence of 6 to 15 deoxynucleotides, wherein the number of the deoxynucleotides of which the base is the adenine (A) is at least 40% of a total number of the deoxynucleotides, and the number of the deoxynucleotides of which the base is the thymine (T) is at least 40% of the total number of the deoxynucleotides;

L2 represents a sequence of 9 to 18 deoxynucleotides;

in the sequence L1 at one end of the linker P1, the deoxynucleotides of which the base is the adenine (A) and the deoxynucleotides of which the base is the thymine (T) are alternately arranged to form a sequence of . . . ATATATAT . . . ; and the sequence L1' at one end of the linker P3 is subjected to pairing hybridization with the sequence L1 of the P1 and is subjected to pairing hybridization with one part of the sequence L2 of the P2.

2. The gold/quantum dot nanoprobe according to claim 1, wherein the linkers P1 and P2 independently contain 18 to 30 deoxynucleotide units, the P3 contains 33 to 42 deoxynucleotide units, and a sequence of 12 to 15 deoxynucleotides of which a base is adenine (A) is positioned in the middle of the P3.

3. The gold/quantum dot nanoprobe according to claim 1, wherein a carbon atom number of alkylene is an integer within a range of 6 to 9, n1 and n2 are integers within a range of 9 to 12, n3 is an integer within a range of 12 to 15, L1 represents a sequence of 9 to 12 deoxynucleotides, and L2 represents a sequence of 12 to 15 deoxynucleotides.

4. The gold/quantum dot nanoprobe according to claim 1, wherein the linkers P1, P2 and P3 have structures in the following table and P1 is P1(a), P1(b), or P1(c), P2 is P(a), P2(b), or P2(c), and P3 is P3(a), P3(b), or P3(c),

| | |
|---|---|
| P1(a) | 5'-SH-$C_6H_{12}$-TTT TTT TTT ATA TAT ATA (SEQ ID NO: 1)-3' |
| P1(b) | 5'-SH-$C_{10}H_{20}$-TTT TTT TAT ATA TAT (SEQ ID NO: 2)-3' |
| P1(c) | 5'-SH-$C_5H_{10}$-TTT TTT TTT TTT CTA TAT ATA (SEQ ID NO: 3)-3' |
| P2(a) | 5'-TAA CAT AAT TAG GTC TTT TTT (SEQ ID NO:4)-$C_6H_{12}$-$NH_2$-3' |
| P2(b) | 5'-TAT CAG TCT GAC TTT TTT (SEQ ID NO: 5)-$C_8H_{16}$-$NH_2$-3' |
| P2(c) | 5'-TAG CAT ATT CTG GCA TTT TTT (SEQ ID NO: 6)-$C_6H_{12}$-$NH_2$-3' |
| P3(a) | 5'-GAC CTA ATT ATG AAAAAAAAAAA TTA TAT ATA TAT (SEQ ID NO: 7)-3' |
| P3(b) | 5'-GTC AGA CTG ATA AAAAAAAAAAAAAAAAA ATA TAT ATA (SEQ ID NO: 8)-3' |
| P3(c) | 5'-TGC CAG AAT ATG AAAAAAAAA CTA TAT ATA TAG (SEQ ID NO: 9)-3'. |

5. The gold/quantum dot nanoprobe according to claim 1, wherein a molar ratio of the P1-AuPNs to the P2-QDs to the P3 is 1:(30 to 70):(100 to 300).

6. A method for detecting active ricin in a sample solution, comprising: (S1) causing a reaction between the gold/quantum dot nanoprobe of claim 1 with active ricin in each of a plurality of solutions, wherein the concentration of active ricin in each solution is known, and obtaining a relationship between the concentration of active ricin and fluorescence intensity at 575 nm ($I_{575}$) by drawing a standard logarithmic curve between the concentration of active ricin and fluorescence intensity at 575 nm; and (S2) adding the gold/quantum dot nanoprobe of claim 1 into the sample solution, monitoring the fluorescence intensity at 575 nm of the sample solution, and determining the concentration of the active ricin in the sample solution according to the relationship obtained in step (S1).

7. A method for visually detecting active ricin in a sample, comprising a step of:
adding the gold/quantum dot nanoprobe according to claim 1 into a sample solution, irradiating the sample solution with an ultraviolet light flashlight, and determining the presence of active ricin in the sample solution when an orange light from the sample solution is visually observed.

8. The gold/quantum dot nanoprobe according to claim 5, wherein the molar ratio of the P1-AuPNs to the P2-QDs to the P3 is 1:(40 to 60):(170 to 220).

9. The gold/quantum dot nanoprobe according to claim 5, wherein the molar ratio of the P1-AuPNs to the P2-QDs to the P3 is 1:(45 to 55):(190 to 210).

10. The gold/quantum dot nanoprobe according to claim 5, wherein the molar ratio of the P1-AuPNs to the P2-QDs to the P3 is 1:50:200.

* * * * *